United States Patent [19]
Carson et al.

[11] Patent Number: 5,541,164
[45] Date of Patent: *Jul. 30, 1996

[54] 2-HALO-2'-DEOXYADENOSINES IN THE TREATMENT OF MONOCYTE-MEDIATED INFLAMMATORY DISEASE CONDITIONS

[75] Inventors: Dennis A. Carson, Del Mar; Carlos J. Carrera, San Diego, both of Calif.

[73] Assignee: The Scripps Research Institute, La Jolla, Calif.

[*] Notice: The term of this patent shall not extend beyond the expiration date of Pat. No. 5,106,837.

[21] Appl. No.: 233,056

[22] Filed: Apr. 26, 1994

Related U.S. Application Data

[60] Division of Ser. No. 838,546, Feb. 19, 1992, Pat. No. 5,310,732, which is a continuation-in-part of Ser. No. 460,351, Jan. 3, 1990, Pat. No. 5,106,837, which is a continuation-in-part of Ser. No. 323,350, Mar. 14, 1989, abandoned, which is a continuation-in-part of Ser. No. 169,618, Mar. 16, 1988, abandoned, which is a continuation-in-part of Ser. No. 825,215, Feb. 3, 1986, abandoned.

[51] Int. Cl.$^6$ ...................................................... A61K 31/70
[52] U.S. Cl. .......................................... 514/46; 536/27.63
[58] Field of Search .................................................. 514/46

[56] References Cited

U.S. PATENT DOCUMENTS

| | | | |
|---|---|---|---|
| 5,106,837 | 4/1992 | Carson et al. | 514/46 |
| 5,310,732 | 5/1994 | Carson et al. | 514/46 |

OTHER PUBLICATIONS

Carrera et al., "Potent Toxicity of 2–Chlorodeoxyadenosine Toward Human Monocytes In Vitro and In Vivo. A Novel Approach to Immunosuppressive Therapy," *J. Clinical Invest.*, 86, 1480–1488 (1990).

Priebe et al., "Selective Modulation of Antibody Response and Natural Killer Cell Activity by Purine Nucleoside Analogues," *Cancer Research*, 48(17), 4799–4803 (1988).

Montgomery et al., "9–(2–fluoro–Deoxy–2–β–D– arabinofuranosyl)guanine: A Metabolically Stable Cytotoxic Analogue of 2'–Deoxyguanosine," *J. Med. Chem.*, 29, 2389–2392 (1986).

Matsuda et al., "Synthesis of a Mutagenic Nucleoside, 2'–Deoxy–2–(p–nitrophenyl)–adenosine," presented at the 14th Symposium on Nucleic Acids Chemistry, *Nucleic Acids, Res. Symposium Ser.*, No. 17, Tokushma, Japan, pp. 141–143 (Nov. 1, 1986).

Christensen et al., "Synthesis and Biological Activity of Selected 2,6–Disubstituted–(2–deoxy–α–and –β–D–erythro–pentofuranosyl)purines," *J. Med. Chem.*, 15(7), 735–739.

Khan et al., "Elucidation of the Mechanism of Selective Inhibition of Mammalian DNA Polymerase Alpha by 2–butylanilinopurines: Development and Characterization of 2–(p–n–butylanmilino)adenine and Its Deoxyribonucleotides," *Nucleic Acids Res.*, 13(17), 6331–6342 (1985).

Parsons et al., "Selective Toxicity of Deoxyadenosine Analogues in Human Melanoma Cell Lines," *Biochem. Pharm.*, 35(22), 4025–4029 (1986).

"Protection de la Liason Glycosidique en Serie Desoxy-2' Adenosine," *Tett. Lett*, 24(1), 53–56 (1983).

Scott, Supplemental European Patent Office Search Report for PCT/US89/01088, Nov. 20, 1990.

Kochetkov et al., *Organic Chemistry of Nucleic Acids*, Part B, Plenum Press, New York, 1972, p. 335.

Singleton et al., *Dictionary of Microbiology and Molecular Biology*, 2nd Ed., John Wiley & Sons, New York, 1987, pp. 513, 562 and 563.

Berkow et al. eds., *The Merck Manual of Diagnosis and Therapy*, 14th Ed., Merck & Co., Inc., 1992, Rahway, N.J., pp. 77–86, 1164–1165, 1305–1314, 1487–1490, 2190–2197.

Sipe et al., "Cladribine [2–CldA] in Treatment of Chronic Progressive Multiple Sclerosis," *The Lancet*, 344, 9–13, (Jul. 2, 1994).

*Primary Examiner*—Douglas W. Robinson
*Assistant Examiner*—L. Eric Crane
*Attorney, Agent, or Firm*—Welsh & Katz, Ltd.

[57] ABSTRACT

Novel adenine derivatives whose structures are represented by Formula I, are disclosed, as are methods of using those compounds and others of Formula II to treat monocyte-mediated disorders such as rheumatoid arthritis and multiple sclerosis.

9 Claims, 7 Drawing Sheets

2-HALO-2'-DEOXYADENOSINES IN THE TREATMENT OF MONOCYTE-MEDIATED INFLAMMATORY DISEASE CONDITIONS

This invention was made with government support under Contract Nos. RR 00833, GM 23200 and CA 01100 by the National Institutes of Health. The government has certain rights in the invention.

This application is a division of application Ser. No. 07/838,546, filed Feb. 19, 1992 now U.S. Pat. No. 5,310,732, that was a continuation-in-part of application Ser. No. 460,351, filed Jan. 3, 1990, now U.S. Pat. No. 5,106,837, that was a continuation-in-part of application Ser. No. 323,350 filed Mar. 14, 1989, now abandoned, that was a continuation-in-part of application Ser. No. 169,618, filed Mar. 16, 1988, now abandoned, that was a continuation-in-part of application Ser. No. 825,215, filed Feb. 3, 1986, now abandoned, all of whose disclosures are incorporated herein by reference.

TECHNICAL FIELD

This invention relates to agents that are useful in the treatment of chronic inflammatory diseases, infection, and autoimmune disorders. More particularly, this invention relates to a compound and a method of treatment for monocyte-mediated diseases or disease states (disorders). In one specific aspect, this invention pertains to a method for treating diseases in which a pathogen resides in monocytes. In a second specific aspect, this invention pertains to the treatment of monocyte-mediated autoimmune disorders, or other chronic inflammatory diseases in which monocyte activation contributes to and thus mediates the pathology of the disease.

BACKGROUND OF THE INVENTION

Recent reports indicate that human immune deficiency virus (HIV) infects macrophages and monocytes in addition to T cells. Levy et al. (1985) Virology, 147:441–448; Gartner et al. (1986) Science, 233:215–219; and Wiley et al., *Proc. Natl. Acad. Sci. USA*, 83:7089–7093 (1986). Acquired immune deficiency syndrome (AIDS) results from infection with HIV, also known as human T-lymphotropic virus Type III (HTLVIII).

AIDS is characterized by extensive immunosuppression that predisposes patients to life-threatening opportunistic infections as well as unusual forms of neoplasm. As to the other known subgroups or types of human T-lymphotropic viruses, Type I (HTLV-I) is believed to cause T cell proliferation in leukemia. The role of HTLV-II in pathogenesis remains unclear, although it has been associated with rare cases of the T cell variant of hairy cell leukemia. Golde et al. (1986), Seminars in Hematol. 23:3–9.

Synthesis of DNA complementary to viral RNA is thought to be required for both retroviral integration into host DNA and for the generation of new virions. For this reason, the HIV-encoded reverse transcriptase is a logical target for the development of agents for the treatment of patients with the acquired immunodeficiency syndrome (De Clercq et al., *J. Med. Chem.*, 29:1561–1569 (1986)], and with other diseases of retroviral origin.

Mitsuya et al. (1985) *Proc. Natl. Acad. Sci. USA*, 82:7006–7100 reported 3'-azido-3'-deoxythymidine (AZT) blocked the replication of HIV in cultured human T lymphoblasts, and inhibited the cytopathic effects of the virus. AZT was presumably phosphorylated by the T cells and converted to the 5'-triphosphate derivative. That derivative was reported by those authors to be an inhibitor of HIV reverse transcriptase activity. Yarchoan et al. (1986) Lancet, 1:575–580, administered AZT to patients with AIDS or AIDS-related disease complexes. The drug was reportedly well tolerated and crossed the blood/brain barrier.

Recently, Mitsuya et al. (1986) *Proc. Natl. Acad. Sci. U.S.A.*, 83:1911–1915 reported that the 2',3'-dideoxynucleoside derivatives of adenosine, guanosine, inosine, cytidine and thymidine also inhibited the infectivity and cytopathic effect of HIV in vitro at concentrations from 10–20 fold less than those that blocked the proliferation of uninfected T cells. These compounds were also reported to be relatively non-toxic towards host T cells. The adenosine and cytidine derivatives were reported to be more potent than the guanosine and inosine derivatives.

The 2',3'-dideoxynucleosides are phosphorylated at the 5'-position in T cells to form the 5'-nucleotide triphosphate derivatives. Those derivatives are well known to be substrates for reverse transcriptase molecules. Ono et al. (1986) *Biochem. Biophys. Res. Comm.*, 2:498–507.

Those 2',3'-dideoxynucleoside 5'-triphosphates are also utilized by mammalian DNA polymerases beta and gamma. Waquar et al. (1984) *J. Cell. Physiol.*, 121:402–408. They are, however, poor substrates for DNA polymerase-alpha, the main enzyme responsible for both repair and replicative DNA synthesis in human lymphocytes. In part, these properties may explain the selective anti-HIV activity of the 2',3'-dideoxynucleosides.

Chan et al. (1982) *J. Cell Physiol.*, 111:28–32 studied the pathways of pyrimidine nucleotide metabolism in murine peritoneal macrophages and monocytes, and reported undetectable levels of deoxycytidine kinase or thymidine kinase in these cells. High levels of adenosine kinase were found, however.

Similar high levels of adenosine kinase have been found in human monocytes and human monocyte-derived macrophages (MDM) in work carried out in the inventors' laboratory. In that preliminary work, MDM were found to exhibit about one-tenth to about one-fourth the nucleoside kinase activity of GEM T lymphoblasts (e.g. ATCC CCL 119) toward uridine, deoxycytidine and thymidine, and about two-thirds the adenosine kinase activity of GEM cells. In addition, that adenosine kinase activity of MDM cells was at least about 10-fold higher than any of the other kinase activities. Those studies also indicated relatively low levels of nucleoside phosphorylation using AZT, dideoxycytidine (ddC) and 2',3'-dideoxyadenosine (ddA) in intact GEM T lymphoblasts and still lower levels with the MDM.

The ability of AZT, ddC and ddA to inhibit synthesis of the p24 (gag) antigen of HIV in GEM and MDM cells was also examined. For GEM cells, the results for all three compounds were similar to those discussed in Mitsuya et al. (1987) *Nature*, 325:773–778 with ddC providing the most inhibitory effect at the lowest concentration, followed by AZT, followed by ddA in a 3-day assay. Using the same concentrations (0.1–100 μM) in a similar 3-day assay, none of those compounds provided any inhibition of p24 (gag) production from MDM cells.

The above results explain in part the observations made in clinical trials with AZT. Those results, in part, have shown that treatment of patients with AIDS or AIDS-related complex with AZT has resulted in elevation of CD4 (T4) peripheral blood cell counts, restoration of cutaneous delayed hypersensitivity, and reduction of the rate of opportunistic infections and death; results that can be related to the effect of AZT on T cells.

However, AZT had no effect on virus isolation rates from peripheral blood cells. That result suggests that a subset of infected cells persists that represents a reservoir of continuing viral replication, and with the above work with MDM cells, indicates that macrophages constitute at least a portion of that in vivo reservoir of HIV.

As noted before, 2',3'-dideoxyadenosine (ddA) inhibits in vitro infectivity and cytopathic effects of HIV. Mitsuya et al. (1986) Proc. Natl. Acad. Sci. U.S.A., 83:1911–1915. However, ddA is a known substrate for adenosine deaminase (also known as adenosine aminohydrolase, EC 3.5.4.4), which converts the compound to 2',3'-dideoxyinosine (ddI) Frederiksen (1966) Arch Biochem. Biophys., 113:383–388. Adenosine deaminase levels in the blood cells of AIDS patients are relatively high compared to normal persons. Thus, in vivo, ddA would be expected to be degraded rapidly to 2',3'-dideoxyinosine, due to the action of endogenous adenosine deaminase. Although 2',3'-dideoxyinosine has anti-HIV activity, it is less potent than AZT or ddA (Mitsuya, 1986, above).

Several 2-substituted adenosine derivatives have been reported not to be deaminated by adenosine deaminase. For example, Coddington (1965) *Biochim. Biophys. Acta*, 99:442–451 reported that deoxyadenosine-1-N-oxide, as well as 2-hydroxy-, 2-methyl-, 2-chloro-, 2-acetamido-, and 2-methylthio-adenosines were neither substrates nor inhibitors for adenosine deaminase. Montgomery, in *Nucleosides, Nucleotides, and Their Biological Applications*, Rideout et al. eds., Academic Press, New York, page 19 (1983) provides a table of comparative $K_m$ and $V_{max}$ data for the deamination of adenosine, 2-halo-adenosines 2-halo-deoxyadenosines and 2-fluoro-arabinoadenosine that also indicates that those 2-halo adenine derivatives are poor substrates for the enzyme relative to adenine itself. Stoeckler et al. (1982) *Biochem. Pharm.*, 31:1723–1728 reported that the 2'-deoxy-2'-azidoribosyl and 2'-deoxy-2'-azidoarabinosyl-adenine derivatives were substrates for human erythrocytic adenosine deaminase, whereas work of others indicated 2-fluoroadenosine to have negligible activity with adenosine deaminase.

2-Chloro-2'-deoxyadenosine is phosphorylated by non-dividing (normal) human peripheral blood lymphocytes and is converted to the 5'-triphosphate. This adenine derivative is not catabolized significantly by intact human cells or cell extracts, and is phosphorylated efficiently by T lymphocytes. Carson et al. (1980) *Proc. Natl. Acad. Sci. USA*, 77:6865–6869.

As discussed before, high levels of adenosine kinase have been found in murine peritoneal macrophages and in human monocytes. Adenosine kinase can phosphorylate 2'-deoxyadenosine derivatives, but does so less efficiently than deoxycytidine kinase. Hershfield et al. (1982) *J. Biol. Chem.*, 257:6380–6386.

In addition to AIDS, other infectious diseases in which pathogenic organisms persist in chronically infected monocytes/macrophages are Chagas' disease and other trypanosomal diseases, Leishmaniasis, mycobacterial infections, systemic and local fungal diseases, and protozoal infections such as toxoplasmosis, malaria and pneumocystis.

Similarly, many autoimmune diseases share common features with the pathogenesis of viral infection. The specific mechanism that mediates autoimmune disorders can be augmented by amplification systems which may involve lymphokines or humoral components.

One form of autoimmune disease involves a cytotoxic mechanism wherein circulating autoantibody reacts with self-antigen present on a cell surface. The cytotoxic process can be mediated by complement or by cells as in antibody-dependent cell-mediated cytotoxicity. The end-result of the cytotoxic mechanism is usually cell lysis, elimination or inactivation, and this is the mechanism of many autoimmune hematologic disorders.

A second form of autoimmune disease involves the formation of immune complexes of autoantibody plus self-antigen that can fix complement as well as initiate inflammatory processes. Organs in which such complexes deposit are subject to inflammation, and ultimately to destruction. Nucleic acids are known to serve as antigens for this mechanism in systemic lupus erythematosus (SLE). Immune complex deposition appears to account for the glomerulonephritis present in many autoimmune disorders.

A third mechanism for autoimmune disorders is mediated by interactions of cells or their soluble products with antigen (cell-mediated immune response) rather than with antibody and complement (humoral immune response). This mechanism is classically manifested in delayed hypersensitivity, which is characterized by a reaction that is time-dependent, has a specific histologic sequence in terms of inflammation and cellular infiltration, and can only be transferred by cells and not by serum.

The effector mechanism of cell-mediated cytotoxicity can include direct cell interaction with antigen or elaboration of lymphokines and monokines. The lymphokines primarily amplify the initial reaction by nonspecifically recruiting inflammatory cells such as neutrophils, cytotoxic T cells, monocytes and macrophages to the reaction area. At that inflammatory site, a cascade effect occurs wherein cells become activated, proliferate and secrete more cytokines.

Rheumatoid arthritis is a chronic recurrent systemic inflammatory autoimmune disease primarily involving the joints. Recent studies have suggested that a virus, possibly Epstein-Barr virus, may be implicated in this autoimmune disorder. The Epstein-Barr virus is a polyclonal stimulator of B cells and can stimulate the production of rheumatoid factors by B cells. In rheumatoid arthritis, there is an increase in alpha$_2$-globulin, a polyclonal hypergammaglobulinemia, and hypoalbuminemia. Cryoprecipitates of immunoglobulins are often seen in rheumatoid vasculitis.

Rheumatoid factors can be present in other autoimmune disorders, as well as in rheumatoid arthritis. Rheumatoid factors have been found to be present in some patients with systemic lupus erythematosus, Sjogren's syndrome, scleroderma and polymyositis.

The deposition of immune complexes on or in the synovia of joints appears to initiate or exacerbate an inflammatory response of the synovial membrane in rheumatoid arthritis. The deposited complexes fix and activate complement, which subsequently stimulates the attraction of inflammatory cells such as monocytes and macrophages. The deeper layers of the synovium are infiltrated by both T and B lymphocytes, plasma cells, monocytes, macrophages and occasionally neutrophils. The infiltrating cells elaborate several effector molecules of the inflammatory response, which transforms the joint fluid into an inflammatory exudate. The immune complexes together with the infiltrating cell-released factors activate the clotting pathway leading to fibrin production and deposition in the joint space, synovium and cartilage.

The essential role of the monocyte in rheumatoid arthritis was confirmed by Fujii et al. (1990) *Ann. Rheum. Dis.*, 49:497–503. Peripheral blood and synovial fluid were obtained from 44 patients with rheumatoid arthritis. The obtained monocytes were examined for their ability to produce interleukin-1β, leucotriene $B_4$, and prostoglandin $E_2$, all factors important in the establishment and maintenance of chronic inflammation. Monocytes derived from the rheumatoid arthritis patients produced significantly more of these factors than monocytes obtained from normal patients, indicating that the monocytes in individuals with rheumatoid arthritis play an important role in mediating the chronic inflammation characteristic of the disease.

Multiple sclerosis (MS) is another monocyte-mediated chronic inflammatory autoimmune disease. Pathologically, MS is the result of demyelination in the brain and spinal cord (central nervous system). Symptoms resulting from this demyelination include weakness, visual impairment, incoordination, and paresthesia (abnormal tingling). The course of the disease is largely unpredictable, but often progresses through a cycle of exacerbation of symptoms followed by remission.

To date, usual treatment consists of therapy with ACTH or corticosteroids such as prednisone. Controlled studies suggest that such treatments induce more rapid clearing of acute symptoms and signs but leave the long-term outcome of the disease unaffected. Long-term maintenance therapy with ACTH or corticosteroids is contraindicated. Evidence indicates that immunosuppreessant agents have no long-term benefit. Cecil, Textbook of Medicine, Beeson et al., eds., 15th ed., W. B. Saunders Company, Philadelphia, (1979) page 847.

Although the exact etiology of MS is unknown, its origins are thought to be autoimmunologic. For example, experimental allergic encephalomyelitis (EAE), an animal model of demyelinating diseases such as MS, is induced by immunizing mice with whole myelin or specific myelin components such as myelin basic protein.

In humans with MS, exacerbations are correlated with high levels of neopterin in blood and cerebrospinal fluid. Neopterin is a factor released from activated monocytes and macrophages, thereby implicating these cells as being involved in MS exacerbations. Fredrickson et al., *Acta Neurol. Scand.*, 75:352–355 (1987); Huber et al., *J. Exp. Med.*, 160:310–316 (1984). Elevated neopterin levels are also found in patients with rheumatoid arthritis.

Indeed, at the microscopic level, monocytes and microglial cells (macrophages of the central nervous system) are found within the demyelinated regions of the nerve cells during MS exacerbations. Beeson et al. (eds.) Cecil Textbook of Medicine, W. B. Saunders Co., Philadelphia, Pa. (1979). As in rheumatoid arthritis, the monocyte plays an important role in mediating the inflammation responsible for MS.

Various usual treatment methodologies have been employed to ameliorate the symptoms of autoimmune disorders such as rheumatoid arthritis and multiple sclerosis. Many of these are directed to use of palliative, anti-inflammatory agents.

Nonsteroidal anti-inflammatory agents, such as phenylbutazone, indomethacin, fenoprofen, ibuprofen, naproxen, sulindac, tolmetin, methotrexate, and mefenamic acid, and antimalarial drugs, such as chloroquine and hydroxychloroquine, have been employed for arthritis, but possess serious side effects upon prolonged usage. Salicylates are commonly employed, specifically aspirin, in dosages from about 3.6 to about 5.4 grams (g) per day. Numerous side-effects are associated with high-dose aspirin therapy such as gastric upset, tinnitus and decreased platelet adhesiveness. Other frequently used palliative anti-inflammatory therapeutic agents such as parenteral gold salts, penicillamine and corticosteroids such as prednisone also possess significant side effects. No treatment to date has had any consistent positive effect on the course of MS.

Recently, the art has described the use of specific deoxyribosides as anti-inflammatory agents. For Instance, U.S. Pat. No. 4,481,197 to Rideout et al relates to the use of unsubstituted 3-deaza-2'-deoxyadenosine derivatives in the treatment of inflammation. U.S. Pat. No. 4,381,344 to Rideout et al. relates to a process for the synthesis of deoxyribosides that utilizes a bacterial phosphorylase.

A deoxyriboside derivative, 2-chloro-2'-deoxyadenosine (CdA), has been found to be an effective agent for the treatment of chronic lymphocytic leukemia and some T cell malignancies. Carson et al. (1984) *Proc. Natl. Acad. Sci. U.S.A.*, 81:2232–2236; Piro et al. (1988), Blood 72:1069–1073. Chronic lymphocytic leukemia is a malignancy of B lymphocytes that bear the Leu-1 surface antigen.

The Leu-1 B cells represent a minor proportion of the normal pool of B lymphocytes, usually less than 20 percent. The Leu-1 B cells express surface markers that are typically found on monocytes (Mac-I antigen) and T-lymphocytes (Leu-1 antigen). Approximately 10 percent of patients with chronic lymphocytic leukemia exhibit accompanying autoimmunity, and recently, Leu-1 B cells have been implicated in the pathogenesis of autoimmune diseases.

Phase 1 studies on humans showed that infusion of increasing doses of 2-chloro-2'-deoxyadenosine [0.1–0.5 milligrams per kilogram of body weight per day (mg/kg/day)] yielded increasing plasma concentrations of the drug [10–50 nanomolar (nM)]. Those infusions indicated that the drug was well tolerated and did not induce nausea, vomiting or fever. The dose-limiting toxicity was bone marrow suppression, which usually occurred at doses greater than about 0.2 mg/kg/day or at 10 plasma levels of greater than about 20 nM.

Other studies, Montgomery et al. (1959) *J. Am. Chem. Soc.*, 82.:463–468, indicated that 2-fluoroadenosine exhibits a relatively high degree of cytotoxicity. Those workers reported that C57 black mice implanted with Adenocarcinoma 755 (Ad755) could tolerate only about 1 milligram per kilogram of body weight. 2-Fluoroadenosine was found to be inactive at that level against Ad755 as well as leukemia L1210 and the Erlich ascites tumor.

U.S. Pat. No. 4,751,221 and its division U.S. Pat. No. 4,918,179 to Watanabe et al. describe the synthesis and use of several 2-substituted-2'-deoxy-2'-fluoroarabino-furanosyl nucleosides including adenine derivatives. Those compounds were said to have anti-tumor and antitrypanosomal biological activities. Cytotoxicity data showing anti-tumor activity of 2-amino-6-thiopurine, guanine and thiopurine derivatives against murine and human cell lines were reported.

U.S. Pat. No. 5,034,518 to Montgomery et al. teaches the synthesis of 2-substituted-2'-deoxy-2'-fluoroaraadenosines. Those compounds were said to have anticancer activity, and data for prolongation of life of mice transplanted with P388 leukemia cells were provided.

Chemotherapeutic agents are described hereinafter that exhibit substantial activity toward resting lymphocytes and monocytes. These agents are also useful in the treatment of autoimmune disorders.

SUMMARY OF THE INVENTION

The present invention contemplates a compound, a composition and a method for treating an infective disorder in which microorganisms reside in infected monocytes, as well as a method for the treatment of inflammation, particularly chronic inflammation that results from monocyte-mediated autoimmune disorders. The compound utilized in the present invention is a substituted 2'-deoxy-adenosine wherein the substituent is at the one, two and/or 2'-positions.

A compound of the invention has a structure that corresponds to that of Formula I:

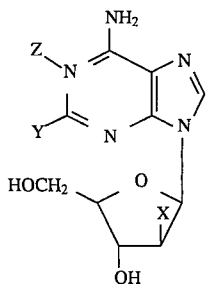

wherein Z is O⁻ or absent,

Y is hydrogen or a substituent containing one to about 20 atoms that is free from net ionic charge at physiological pH values, provides a soluble adenine derivative and whose presence on the adenine moiety inhibits deamination of the adenine derivative by adenosine deaminase; and X is hydrogen or fluoro; with the provisos (i) that when Z is absent, Y is lower alkyl or hydroxyl; and (ii) Y is hydrogen only when Z is present and X is fluoro.

A composition of the present invention contains a sufficient amount of one, or more, of the above compounds of Formula I, dissolved or dispersed in a pharmacologically acceptable carrier, to provide a therapeutically effective dose, as discussed hereinafter. Depending upon the treatment modality, the monocyte cells are contacted as discussed below with a compound of Formula I at a typical concentration of about 0.5 nanomolar (nM) to about 50 micromolar (µM), more preferably at about 10 nM to about 10 µM.

A method of treating a monocyte-mediated disorder is contemplated. In this method, monocytes are contacted with a composition containing a pharmacologically acceptable carrier that itself contains dissolved or dispersed therein a substituted adenine derivative having a structure that corresponds to that of Formula II as an active ingredient or agent, either alone or in combination with an antimicrobial agent. The substituted adenine derivative and the antimicrobial agent, when present, are each present in an amount sufficient to provide a therapeutically effective dose over the period of contacting. The monocytes are contacted in vivo by administration of the composition to a mammal such as a human. In vitro contact is achieved by admixing the composition with a preparation of monocytes.

A substituted adenine derivative of Formula II has a structural formula corresponding to:

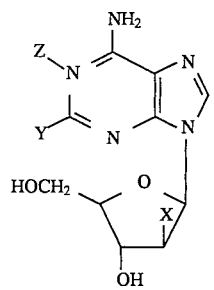

wherein Z is O⁻ or absent,

Y is hydrogen or a substituent containing one to about 20 atoms that is free from net ionic charge at physiological pH values, provides a soluble adenine derivative and whose presence on the adenine moiety inhibits deamination of the adenine derivative by adenosine deaminase; and X is hydrogen or fluoro, with the proviso that Y is hydrogen only when Z is present.

Particularly preferred compounds of Formula II are free of the Z group; i.e, Z is absent, and contain a halo group at the 2-position. Most preferred are 2-chloro-2'-deoxyadenosine and 2-chloro-2'-deoxy-2'-arafluoroadenosine.

This method of treatment decreases the level of infected monocytes in the blood as a result of the specific cytotoxicity of the compounds utilized toward monocytes. Additionally, when an antimicrobial agent is used in combination with an above compound of Formula II, that antimicrobial agent directs its action against the causative microorganism itself.

In one aspect, a method of treating an infective disorder in which microorganisms reside in monocytes is contemplated. Usually, the monocytes are chronically infected. A mammal afflicted with such a microbial infective disorder is administered in vivo with a composition as discussed above.

A particular method of treatment for a viral infection disorder is contemplated in the present invention in which a mammal affected with a viral infection is treated with an effective therapeutic dosage of a compound of Formula II either alone or in combination with another antiviral agent, administered either together or separately, with a pharmacologically acceptable carrier. Preferred disorders for treatment are those in which the infective virus is localized in monocytes prior to cell lysis and viral release into the circulation.

The present invention also contemplates a method for the treatment of inflammation, particularly chronic monocyte-mediated inflammation as occur during autoimmune disorders such as rheumatoid arthritis and multiple sclerosis, by the suppression or killing of monocytes. Here, a composition containing a compound whose structure corresponds to that of Formula II, as discussed above, is again used.

In this embodiment, a warm-blooded animal with inflammation is administered an amount of the above-described composition containing a compound of Formula II present in an amount sufficient to provide a therapeutically effective dose. Exemplary dosages range from about 0.04 to about 1.0 mg/kg/day, with dosages of about 0.04 to about 0.2 mg/kg/day being more preferred. Typically, the amount is sufficient to provide a concentration in the animal's plasma of about 0.5 nanomolar (nM) to about 50 nM, more preferably of about 1 nM to about 10 nM. This method is particularly useful for the treatment of rheumatoid arthritis and multiple sclerosis in humans.

Preferably, the agent contemplated for use in the present invention is a 2-halo-2'-deoxyadenosine (2-halo-2'-deoxy-9, 1'-beta-ribofuranosyladenine) or a 2-halo-2'-deoxy-2'-arafluoroadenosine, and most preferably the halo group is chloro.

A further aspect contemplated by the present invention comprises the peroral administration of an effective amount of the active ingredient (agent) of the invention in a method of treating disease. Here, a compound of Formula II is utilized in which X is fluoro.

In each of the before-described methods, the substituted 2'-deoxyadenosine derivative is administered in a therapeutically effective amount. The effect of a compound of Formula II is both time and dose dependent. As a consequence, one can tailor the dosage and duration for which a particular compound is administered to the illness being treated and the condition of the treated host mammal, such as a human. Thus, for treatment of an inflammatory disorder, impairment of monocyte function can suffice to provide relief, and an amount sufficient to provide such impairment is one measure of a therapeutically effective amount. Where the disease state or condition to be treated is more severe, or life-threatening, treatment is more aggressive, and a therapeutically effective amount is an amount that is sufficient to kill at least 50 percent of the monocytes present but is less than that which substantially impairs bone marrow function as determined by usual procedures when administration is in vivo. The monocyte killing amount of a compound of Formula II is another measure of a therapeutically effective dose and monocyte death is measured at a time seven days after the initial administration.

The present invention has several benefits and advantages.

One benefit is that use of one of its methods can eliminate monocyte-borne pathogens from the body of an infected animal.

An advantage of the present invention is that use of one of its methods can substantially reduce inflammation caused by inflammatory diseases such as rheumatoid arthritis.

Still another advantage of the invention is that its methods can be practiced by oral administration.

Still further benefits and advantages of the invention will be apparent to those skilled in the art from the description that follows.

BRIEF DESCRIPTION OF DRAWINGS

In the drawings forming a portion of this disclosure.

DETAILED DESCRIPTION OF THE INVENTION

Figure 1:
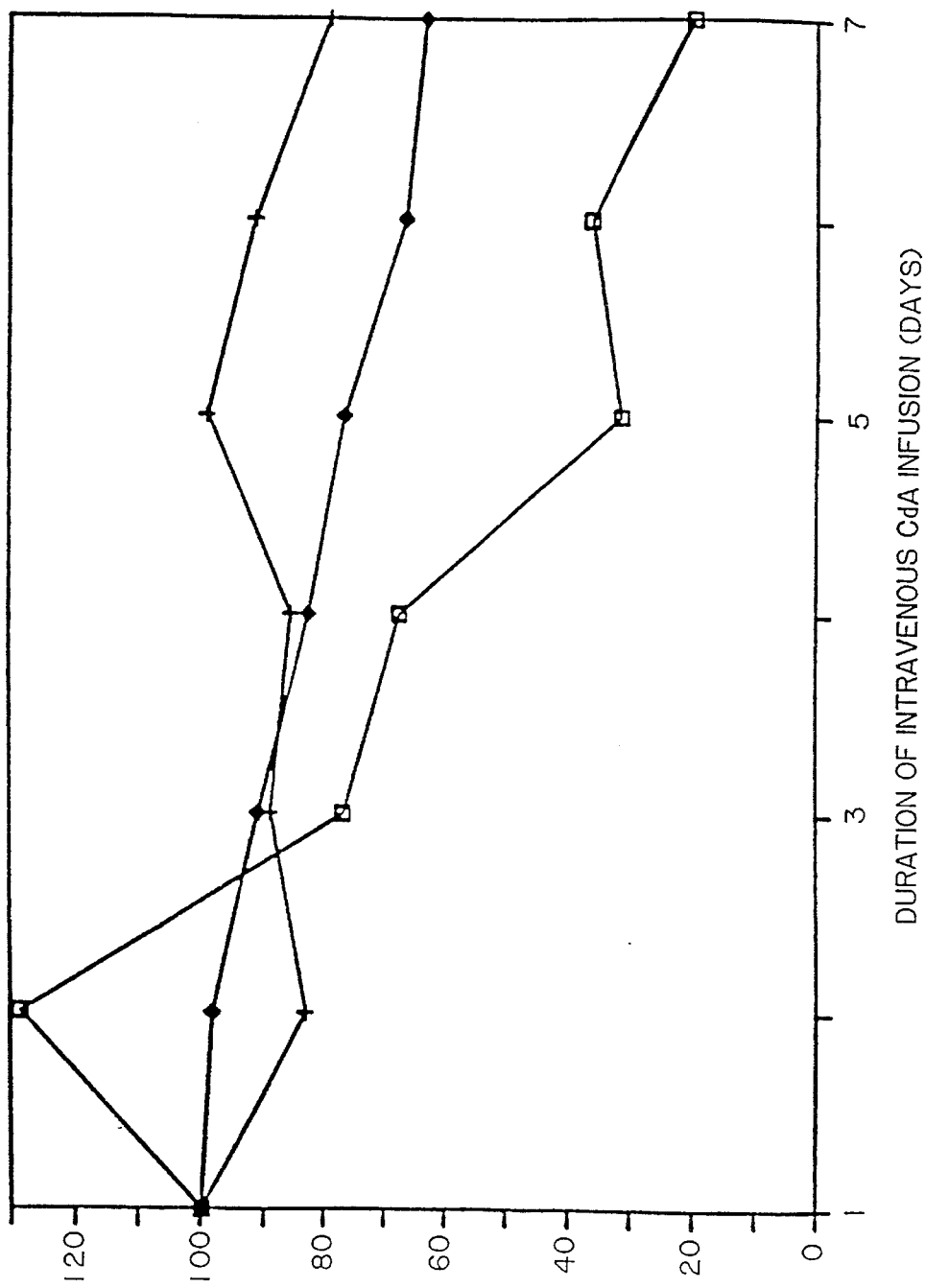
FIG. 1 is a graph showing the results of a study of the cytotoxicity of 2-chlorodeoxyadenosine (CdA) toward three cell types in the peripheral blood of eight cutaneous T-cell lymphoma patients. A continuous intravenous infusion of CdA (0.1 mg/ml in isotonic saline) was administered to each patients at a dosage of 0.1 mg/kg per day, with the patients receiving therapy for seven days. Blood samples were removed daily and cell counts performed, with averaged values being shown. Graph symbols are as follows: open squares indicate the monocytes; plus signs indicate neutrophils ($\times 10^{-1}$); and closed diamonds indicate lymphocytes. The cell concentration (ordinate) is plotted for the day of treatment (abscissa) on which it is measured.

The present invention contemplates a compound, a composition containing that compound and a method of using a composition of the invention, or another composition, for treating a monocyte-mediated disorder. It is to be understood that the monocytopenia and inhibition of monocyte function discussed hereinafter using a method of the invention were quite unexpected.

Those results were particularly unexpected in view of the recently published work of Urba et al. (1989) Blood, 73:38–46 and Bakul et al. (1989) Cancer, 63:14–22 who treated patients with hairy cell leukemia, another disease in which a method similar to that disclosed herein is useful. Those treatments utilized deoxycoformycin together with interferon alpha-2a, or deoxycoformycin alone, respectively.

Deoxycoformycin is an irreversible inhibitor of adenosine deaminase, and its use causes adenosine and deoxyadenosine to accumulate in the cells, much the same as an adenine derivative useful herein accumulates in the cells. Lymphocytopenia and DNA strand breaks observed by the treatment are believed to be mediated by accumulation of deoxyadenosine nucleotides.

Urba et al. reported that specific lymphocytes bearing the CD4 and CD8 markers decreased during treatment. Bakul et al. studied absolute counts of cells from their patients, and reported a general decrease in numbers during treatment. Both groups, however, reported an increase in monocyte levels during treatment.

Thus, although deoxycoformycin irreversibly inhibits adenosine deaminase and permits an accumulation of adenosine and deoxyadenosine, a result similar to that which occurs by use of a method of this invention, administration of deoxycoformycin results in an increase in monocyte levels during treatment, whereas treatment using a method of this invention causes at least impairment of monocyte function or monocytopenia (monocyte death), as is discussed hereinafter. Those differences in monocyte-specific activity coming from a similar initial event, i.e., accumulation of adenosine or deoxyadenosine or a derivative as herein described, is quite startling and unexpected.

A. Compounds

A compound contemplated in the present invention is a substituted-2'deoxy-arabinofuranosyladenine (substituted adenine) derivative whose structure is represented by Formula I:

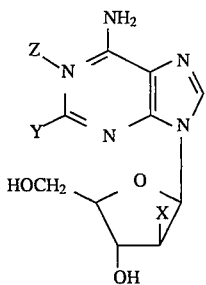

wherein X is either fluorine or hydrogen;

Z is an oxide radical (O⁻) or is absent; and

Y is hydrogen or a radical containing one to about twenty atoms that is free from net ionic charge at physiological pH values, provides a soluble adenine derivative, and whose presence on the adenine moiety inhibits deamination of the adenine derivative by adenosine deaminase, and preferably is a member of the halogen group constituted by fluorine, chlorine and bromine;

with the provisos that (i) when Z is absent, Y is lower alkyl or hydroxyl; and (ii) Y is hydrogen only when Z is present and X is fluoro.

Preferably, Y is chloro. Other Y substituents are selected from the group consisting of lower alkyl, lower alkanoylamido, lower alkylthio and hydroxyl radicals. In particularly preferred embodiments, when Y is chloro, X is fluorine.

Of the compounds of Formula I, those where X is fluoro are particularly preferred for use by oral administration.

Illustrative of compounds of Formula I are the following arabinofuranosyl derivatives of adenine:

2-methyl-9,1'-beta-2'-deoxy-2'-fluoro-D-arabinofuranosyladenine;

2-isopropyl-9,1'-beta-2'-deoxy-2'-fluoro-D-arabinofuranosyl-adenine;

2-hydroxy-9,1'-beta-2'-deoxy-2'-fluoro-D-arabinofuranosyladenine;

2-chloro-9,1'-beta-2'-deoxy-2'-fluoro-D-arabinofuranosyladenine-1-N-oxide;

2-fluoro-9,1'-beta-2'-deoxy-2'-fluoro-D-arabinofuranosyladenine-1-N-oxide;

2-bromo-9,1'-beta-2'-deoxy-2'-fluoro-D-arabinofuranosyladenine-1-N-oxide;

2-methyl-9,1'-beta-2'-deoxy-2'-fluoro-D-arabinofuranosyladenine-1-N-oxide;

2-(N-acetamido)-9,1'-beta-2'-deoxy-2'-fluoro-D-arabinofuranosyladenine-1-N-oxide;

2-hydroxy-9,1'-beta-2'-deoxy-2'-fluoro-D-arabinofuranosyladenine-1-N-oxide;

2-(2-methylbutyl)-9,1'-beta-2'-deoxy-2'-fluoro-D-arabinofuranosyladenine-1-N-oxide;

2-fluoro-9,1'-beta-D-2'-deoxyadenosine-1-oxide; and 2-chloro-9,1'-beta-D-2'-deoxyadenosine-1-oxide.

A compound from a somewhat broader group of adenine derivatives is useful in a method of this invention. A compound of that broader group has a structure that is represented by Formula II:

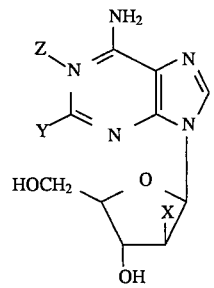

wherein Z is an oxide radical (O⁻) or is absent;

Y is hydrogen or a radical containing one to about twenty atoms that is free from net ionic charge at physiological pH values, provides a soluble adenine derivative, and whose presence on the adenine moiety inhibits deamination of the adenine derivative by adenosine deaminase; and X is hydrogen or fluorine, with the proviso that Y is hydrogen only when Z is present.

The compounds represented by Formula I are included among the compounds of Formula II as are additional compounds. Preferred additional compounds included in Formula II but not in Formula I are:

2-chloro-9,1'-beta-D-2'-deoxyribosyladenine (2-chloro-deoxyadenosine; CdA);

2-bromo-9,1'-beta-D-2'-deoxyribosyladenine; 2-methyl-9,1'-beta-D-2'-deoxyribosyladenine; 2-fluoro-9,1'-beta-D-2'-deoxyribosyladenine; 2-acetoamido-9,1'-beta-D-2-deoxyribosyladenine; 2-methylthio-9,1'-beta-D-2'-deoxyribosyladenine; 2-chloro-9,1'beta-2'-deoxy-2'-fluoro-D-arabinofuranosyl-adenine; 2-bromo-9,1'-beta-2'-deoxy-2'-fluoro-D-arabinofuranosyl-adenine; 2-(N-acetamido)-9,1'-beta-2'-deoxy-2'-fluoro-D-arabinofuranosyladenine; 2-methylthio-9,1'-beta-2'-deoxy-2'-fluoro-D-arabinofuranosyladenine.

Inasmuch as the X, Y and Z substituents of a compound of both Formula I and Formula II can be the same, and the compounds of Formula I are encompassed in Formula II, albeit the provisos that constitute portions of these formulas are different, the discussion that follows is intended to apply to a compound from both formulas.

It is noted that when X is hydrogen the sugar ring can be named as a 2'-deoxyribosyl or 2'-deoxyarabinofuranosyl radical. Both nomenclatures are utilized herein. When the class of compounds embraced by Formula I or Formula II is discussed, all of the compounds are considered herein as derivatives of arabinose. However, when specific compounds of the subclass where X=H are discussed, the more familiar deoxyribose nomenclature is used, such as in deoxyadenosine. These compounds are also referred to herein more simply as an adenine derivative.

In the above formulas, and in all other formulas shown herein, hydrogen atoms on the purine and furanosidyl rings that are not needed to show conformation about a particular bond are not shown. Thus, the 7-position adenine hydrogen is not shown.

It is also to be understood that the D isomers of compounds of the formulas are the isomers contemplated. It is further to be noted that the designation "halo" used herein is meant to include fluorine, chlorine and bromine derivatives, and to exclude iodine derivatives, which are unstable and decompose, and astatine derivatives that are radioactive. Where specific halogen derivatives are intended, those compounds are named specifically.

As used herein, "a substituent free from net ionic charge" includes both charged and uncharged radicals, wherein when the substituent radical is charged, an internal zwitterionic charge pair is present that results in the absence of a net ionic charge for the molecule at physiologic pH values. N-oxide compounds are exemplary of such substituents.

As used herein, a "soluble adenine derivative" is an adenine derivative which is able to dissolve and remain soluble in a body fluid such as blood at a therapeutically effective dose as is discussed hereinafter.

As used herein, a "substituent whose presence on the adenine moiety inhibits deamination of an adenine derivative by adenosine deaminase" is one that, when 100 microliters of a 1 millimolar solution of the substituted adenine derivative is incubated for three hours at room temperature with 25 units of calf spleen adenosine deaminase (1 unit catalyzes the deamination of 1 micromole of adenosine per minute), produces a single UV-absorbing spot upon cellulose-thin layer chromatography of the reaction mixture whose $R_f$ value is the same as that of the substituted adenine derivative used.

The metabolism of a compound by adenosine deaminase can be investigated by the following procedure. The individual nucleosides, at concentrations from 5–200 μM in 10 mM sodium phosphate, pH 7.5, are incubated at 18–20 degrees C. with 0.01 EU/ml calf intestinal adenosine deaminase. The change in the optical density at 265 nm and 250 nm is monitored spectrophotometrically. The $K_m$ and $V_{max}$ values are determined by the Lineweaver-Burke method, utilizing the $\Delta E^M_{265}$ between adenosine and inosine.

The ratio $V_{max}/K_m$ also provides a measure of relative efficiency of deamination by the enzyme. A substituent that provides a $V_{max}/K_m$ ratio that is about 1 percent or less than that for the ratio obtained using 2'-deoxyadenosine is also a "substituent whose presence on the adenine moiety inhibits deamination of an adenine derivative by adenosine deaminase."

As used herein, lower alkyl radicals include $C_1$–$C_6$ straight chain, branched and cyclic alkyl groups, for example, methyl, ethyl, n-butyl, t-butyl, n-hexyl, 1-ethylbutyl, cyclopentyl, cyclohexyl and the like. Lower alkanoylamido radicals include $C_1$–$C_6$ radicals, for example, formamido, acetylamido, propionamido, hexamoylamido and the like. Lower alkylthio radicals include $C_1$–$C_6$ straight chain, branched and cyclic alkyl groups as discussed above linked to a thio radical.

The pharmacologically acceptable salts of a compound of Formula I or Formula II are also utilized. The phrase "pharmacologically acceptable salts," as used herein, refers to non-toxic acid addition salts that are generally prepared by reacting a compound with a suitable organic or inorganic acid. Representative salts include the hydrochloride, hydrobromide, sulfate, phosphate, citrate, acetate, maleate and the like.

B. Compositions

A compound of Formula I dissolved or dispersed in or together with a pharmacologically acceptable carrier constitutes a composition of this invention. However, since a compound of Formula I is embraced by Formula II, and a composition containing a compound of Formula II is useful in a method of the invention, a composition containing a compound of Formula I will frequently be discussed hereinafter in terms of a composition of a compound of Formula II.

A compound of Formula II and its pharmacologically acceptable salts are useful in both short and long term treatment. For instance, a 2-substituted-9,1'-beta-2'-deoxy-2'-fluoro-D-arabinofuranosyladenine is administered to the warm-blooded animal internally, e.g., parenterally, orally, or rectally as a suppository, in an effective amount.

Although a compound of Formula II and its pharmacologically acceptable salts can be administered as the pure chemical, it is preferred that it be administered as a pharmaceutical composition. In either event, it is administered in an amount sufficient to provide a therapeutically effective dose as is discussed hereinafter.

Accordingly, the present invention utilizes a pharmaceutical composition comprising a therapeutically effective dose of a compound of Formula I or Formula II, preferably wherein X is fluoro, or a pharmacologically acceptable salt thereof, hereinafter referred to as the "active ingredient" or "agent," dissolved or dispersed in a pharmacologically acceptable carrier or diluent.

A pharmaceutical composition is prepared by any of the methods well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of Formula II can be utilized in liquid compositions such as sterile suspensions or solutions, or as isotonic preparations containing suitable preservatives. Particularly well-suited for the present purposes are injectable media constituted by aqueous injectable isotonic and sterile saline or glucose solutions. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles.

The agents can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods to form liposomes are known in the art. See, for example, Prescott, Ed., *Methods in Cell Biology*. Volume XIV, Academic Press, New York, N.Y. (1976), p. 33 et seq.

An agent of Formula II can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

Oral administration of the compound is a particularly attractive mode of administration. One drawback usually associated with oral administrations of bioactive nucleoside compounds, however, is their potential decomposition in the acidic conditions of the stomach. That is, the glycosidic bond tends to hydrolyze under acid conditions.

However, where oral administration is desired, substitutions on the 2-position of the adenine ring of the compound of Formula II are utilized along with a 2'-fluoro-substituted arabinofuranosidyl ring.

Marquez et al. (1987) *Biochem. Pharm.*, 36:2719–2722 reported preparation of 2'-fluoro-2',3'-dideoxyribose and 2'-fluoro-2',3'-dideoxyarabinose derivatives of adenine. Their findings stated that both derivatives were stable at a pH value of 1 at 37 degrees C., whereas dideoxyadenosine had a half-time of 35 seconds under those conditions.

The ability of an adenine derivative to be or not to be a substrate for adenosine deaminase is more a function of the 2-substituent or lack thereof on the adenine portion of the molecule than a function of substituents on the linked sugar ring portion, at least as far as the substituents on both rings herein are concerned.

C. Methods

As noted earlier, a method of treating a monocyte-mediated disorder is contemplated herein. Broadly in that method, monocytes are contacted with a composition containing a pharmacologically acceptable carrier having dissolved or dispersed therein, as an active ingredient, a substituted adenine derivative (substituted 2'-deoxy-adenosine) whose structure corresponds to that of previously discussed Formula II. That agent of Formula II can be present alone or in combination with an antimicrobial agent, as a second active ingredient (agent). The substituted adenine derivative, and the antimicrobial agent when present, are each present in the composition in an amount sufficient to provide a therapeutically effective dose over the period of contacting. The above treatment is typically repeated periodically such as weekly or monthly over a time period of several months to about one year.

It is particularly contemplated that contact between the monocytes and agent of a composition be in vivo. However, in vitro contact as is illustrated hereinafter and as can be achieved by well known extracorporeal methods are also contemplated.

The phrase "monocyte-mediated" is used herein to mean that monocytes or cells of the monocyte lineage such as macrophages are involved in the disease or condition, collectively referred to as the "disorder," to be treated. The degree of monocyte involvement in a given disorder is a function of that disorder and can be different for different types of disorders. For example, in the case of microbial (bacterial, parasitic, viral, and the like) disease, the monocytes harbor the microbes and can shield them from treatment with usual drugs. In the case of inflammatory disorders such as arthritis, the monocytes and/or macrophages accumulate at the site of inflammation, and contribute to the disorder through one or more mechanisms such as phagocytosis, and release of hydrolytic enzymes and cytokines, such as IL-6, release of fever-inducing protein, such as IL-1, and walling off of the inflamed area.

A method for the treatment of infective disorders in which microorganisms such as viruses, bacteria, parasites, or the like reside in chronically infected monocytes is contemplated as a specific embodiment of the present invention. The treatment of viral infections, and especially T-lymphotropic viral infections and disorders in which the infective virus is localized in monocytes of an affected mammal is a particular aspect of the present invention. Such affected mammals are preferentially human patients.

Thus, a composition containing a compound of Formula II is administered either alone or in combination with an antimicrobial agent to a mammal affected with such a microbial disorder in amounts sufficient to provide a therapeutically effective dose of each drug to the mammal. The antimicrobial agent is administered to the mammal either together with or separately from the administration of the composition containing a compound of Formula II. The composition is maintained within the mammal until its constituent components are eliminated by usual bodily processes.

The amount of a compound of Formula II present in a composition and used in a method as described above is a function of several variables, as is well known in the medicinal arts. Among those variables are whether the administration is in vivo or in vitro, if in vitro, the number of cells to be treated that are present, the animal treated, the disease to be treated in the animal or cells, and also the method of administration. Exemplary concentrations are illustrated hereinafter for both in vivo and in vitro uses.

Regardless of the above variables, in disorders where a microorganism is known to be involved such as those discussed before and immediately hereinafter (non-inflammatory disorders or those other than autoimmune-related disorders) the substituted 2'-deoxyadenine derivative is administered in an amount that is sufficient to kill at least about 50 percent of the monocytes present over the duration of the treatment. Preferably, about 90 to 100 percent of the originally present monocytes are killed.

When the administration is in vivo, the amount administered is less than that which substantially impairs bone marrow functions as determined by usual procedures. When the administration is in vitro as in an extracorporeal administration to an animal such as a human where the 2'-deoxyadenine derivative does not substantially enter the body of the treated animal, a limiting concentration is that which is not prohibitively cytotoxic to other cells that may be present.

An amount sufficient to kill at least about 50 percent of the monocytes originally present while not substantially impairing bone marrow function over the course of the administration of the agent is one way of defining a therapeutic dose.

The above amount of a 2'-deoxyadenine derivative of Formula II or its pharmacologically acceptable salt present in the composition is also an amount sufficient to provide about 0.04 to about 1.0 mg/kg of body weight of the treated host mammal per day, more preferably about 0.04 to about 0.20 mg/kg/day, more preferably still at about 0.05 to about 0.15 mg/kg/day and most preferably about 0.1 mg/kg/day, when given in vivo. This amount is another way of defining a therapeutically effective dose that is particularly useful when a compound of Formula II is administered by infusion.

The molar plasma concentration of the compound of Formula II or the pharmacologically acceptable salts thereof during treatment is preferably in the range of about 1 nanomolar (nM) to about 100 nM, particularly about 5 nM to about 50 nM, and more preferably about 10 nM to about 20 nM. Molarity of the 2'-deoxyadenine derivative in plasma of the treated (administered to) animal thus provides still another measure of a therapeutically effective dose from which the amount in a composition can be calculated.

It is to be understood that the above therapeutically effective dosages need not be the result of a single administration, and are usually the result of the administration of a plurality of unit doses. Those unit doses can in turn comprise portions of a daily or weekly dosage, and thus, the therapeutically effective dose is determined over the period of treatment (contacting).

Oral administration is the preferred mode of administration for the 2'-fluoroadenine derivatives, as already noted. To achieve the desired plasma concentration of the agent, a range of doses can be employed depending upon the specific mode of administration, objective of the particular treatment, the particular compound being used, and like considerations.

For example, for oral administration, the daily dose can be about 0.04 to about 1.0 mg/kg of body weight, more preferably about 0.04 to about 0.20 mg/kg/day, more preferably still at about 0.05 to about 0.15 mg/kg/day, and most preferably about 0.1 mg/kg body weight. In general, the amount of active substituted adenine derivative administered can vary over a relatively wide range to achieve, and preferably maintain, the desired plasma concentration.

Unit dosage forms of the adenine derivative can contain about 0.1 milligrams to about 15 milligrams thereof. A preferred unit dosage form contains about 0.1 to about 1 milligram of agent and can be administered 2 to 5 times per day. However, it should be noted that continuous infusion at a rate designed to maintain the above described plasma concentration is also contemplated.

Duration of a particular treatment can also vary, depending on severity of the disease, whether the treatment is intended for an acute manifestation or for prophylactic purposes, and like considerations. Typical administration lasts for a time period of about 5 to about 14 days, with a 7-day time course being usual. Courses (cycles) of administration can also be repeated at monthly intervals, or parenteral unit dosages can be delivered at weekly intervals. Oral unit dosages can be administered at intervals of one to several days to provide the determined therapeutically effective dose. Thus, in vivo administration of a before-discussed dosage over a time period of about 5 to about 14 days or at weekly or daily intervals provides an amount sufficient to kill at least about 50 percent of the originally present monocytes.

This method of treatment produces a decrease in the level of monocytes in the blood due to the toxicity of the utilized compounds of Formula II toward monocytes. This method can be used to reduce the number of monocytes circulating in a treated mammal's blood stream by about 90 percent of the number present prior to treatment over a seven day treatment period with the level of circulating monocytes returning to pretreatment levels about two weeks after the treatment stopped. This exemplary study is illustrated hereinafter.

The combination therapy methodology of the present invention focuses therapeutic agents against both the causative infective agent and the monocyte host. Examples of particular diseases that are amenable to this treatment (and parenthesized therapeutic agents currently utilized in their treatment) in humans are the following:

| | |
|---|---|
| Chagas' disease | (nifurtimox) |
| Leishmaniasis | (stibogluconate; amphotericin B; pentamidine isethionate) |
| Toxoplasmosis | (pyrimethamine; sulfonamide) |
| Malaria | (chloroquine; primaquine; pyrimethamine; mefloquine) |
| Pneumocystis | (trimethoprim sulfamethoxazole; pentamidine isethionate) |

Therapeutic amounts and treatment regimens for the above-noted parenthesized therapeutic agents are well known, and can be readily obtained from usual sources such as the *Physicians Desk Reference*, 42 ed, Medical Economics Corp., Oradell, N.J. (1988).

In an exemplary embodiment, a patient afflicted with a Leishmaniasis is treated in the method of the present invention. The patient receives a composition containing a compound of Formula II at a therapeutically effective dose, together with the administration of pentamidine. In a particularly preferred embodiment, the patient is perorally administered a composition containing 0.15 mg/kg/day of 2-chloro-9,1'-beta-2'-deoxy-2'-fluoro-D-arabinofuranosyladenine in a pharmacologically acceptable carrier, and receives 4 mg/kg/day of pentamidine by intramuscular injection, for a period of about 7 days.

Other diseases of uncertain etiology wherein the monocyte/macrophage is believed to be involved are sarcoidosis, chronic granulomatous hepatitis, Wegener's granulomatosis, Paget's disease, atherosclerosis, inflammatory bowel disease, and granulomatous uveitis. These diseases are currently treated principally with steroids, such as prednisone, or etidronate (Paget's disease) or sulfasalazine (granulomatous uveitis).

In the treatment of a viral infection, human patients or lower animals such as laboratory animals like mice, rats, chimpanzees and the like, and veterinary animals such as dogs, cats, cattle, sheep, pigs and the like are administered a composition containing a compound of Formula II either alone or in combination with another antiviral therapeutic agent in amounts sufficient to provide therapeutically effective doses of one or both drugs, as is applicable.

In an exemplary treatment methodology, patients affected with AIDS are treated with a combination of azidothymidine (AZT), dideoxyinosine (ddI), dideoxycytidine (ddC), interferon, acyclovir and the like, and a substituted-2'-deoxyarabinofuranosyladenine derivative such as 2-chlorodeoxyadenosine (CdA) or 2-methyl-9,1'-beta-2'-deoxy- 2'fluoro-D-arabino-furanosyladenine (CAFdA). AZT combination therapy has recently been utilized in the treatment of AIDS, wherein lower dosages of AZT are administered together with reduced dosages of a second chemotherapeutic agent, as detailed in AIDS/HIV *Experimental Treatment Directory*, [American Foundation for AIDS Research (1988)]. For example, the patients receive a therapeutically effective dosage of AZT (about 200 mg orally every four hours) for four weeks, together with about 0.04 to about 1.0 mg/kg of body weight per day of CdA for about 5 to about 14 days, and typically for about 7 days.

The administration of the CdA (or an analogous compound of Formula II) produces a dramatic decrease in blood monocytes, in which the virus is harbored, as a result of the compound's enhanced toxicity towards monocytes. The concomitant administration of AZT (or another antiviral agent) kills viruses (or inhibits viral replication) by entering cells that are invaded by the viruses and presumably incorporating into growing DNA chains resulting in termination of the chains and subsequent inhibition of viral replication within these cells and further infection.

The combination treatment methodology of the present invention is thus effective against both active virus that invades cells and latent virus present in monocyte host cells. Additional therapeutic agents for treating HIV and appropriate dosages of administration can be found in AIDS/HIV Experimental Treatment Directory, above.

By the term "inflammation" is meant the reactive state of hyperaemia and exudation from its blood vessels, with consequent redness, heat, swelling and pain, which a tissue enters in response to physical or chemical injury or bacterial invasions. Such inflammations are mediated by monocytes, and other phagocytes, and are typically chronic.

Clinical conditions with which monocytemediated inflammation is associated, and hence for which an anti-inflammatory agent is indicated, include, for example, arthritis, including rheumatoid arthritis, multiple sclerosis and osteoarthritis, post-operative inflammation, dental inflammation, and acute and chronic ocular inflammatory diseases such as conjunctivitis.

There is provided as a further aspect of the present invention a method for the treatment of inflammation, particularly that which occurs during autoimmune disorders that include a cellular autoimmune response. The method comprises administration of a composition as previously described in an amount sufficient to provide a therapeutically effective dose of a compound of Formula II or a pharmacologically acceptable salt thereof. Preferably, that administration is by the oral route and X is fluoro.

A dosage over a time period described previously for non-autoimmune-related conditions can also be used for treatment of inflammation due to a monocyte-mediated autoimmune response. Such a treatment although effective is, however, quite aggressive and can leave the treated host animal in an unnecessarily immunocompromised state.

A less aggressive treatment regimen is also therefore contemplated. Here, a before-described dosage, e.g., plasma concentration, is again utilized, but for a shorter contact time course so that monocyte function is impaired, but the monocytes are not substantially killed as is the result of the before-discussed treatment regimen. Impairment of monocyte function is herein defined as a reduction of at least about 25 percent in the spontaneous secretion of interleukin-6 (IL-6) by monocytes cultured in the presence of a compound of Formula II for a time period of 72 hours. A useful assay for monocyte impairment is discussed hereinafter.

In an exemplary treatment regimen, a compound of Formula II is administered in an amount of about 0.04 to about 1.0 mg/kg/day, more preferably about 0.04 to 0.20 mg/kg/day, more preferably still about 0.05 to about 0.15 mg/kg/day, and most preferably about 0.1 mg/kg/day. Such treatments typically provide a plasma concentration of about 0.5 nM to about 50 µM, and more preferably about 10 nM to about 10 µM. That single administration is repeated periodically such as weekly over a time period of several months, e.g. about three to about nine months. In usual practice, treatments are administered over a period of about five to seven days and are repeated at about three to about four week intervals for several months, e.g. about three to about nine months.

Such an administration can be carried out on an outpatient basis for humans using an intravenous infusion lasting about 2 to about 4 hours in a doctor's office. As such, the treatment is far less invasive than is a continuous infusion over a period of several days that usually requires a hospital stay for the host mammal; i.e., human patient. A less invasive continuous infusion method that employs a pump linked to a catheter that automatically infuses a predetermined dosage permits the patient to be ambulatory during the infusion.

Conditions where the suppression of the inflammatory immune response is desirable include autoimmune diseases such as rheumatoid arthritis, multiple sclerosis, systemic lupus erythematosus, hemolytic anemia, ulcerative colitis, nephrosis and the prevention of rejection of foreign cells such as grafts including organ transplants.

It is to be understood that any of the before-described treatment regimens can be utilized for any of the monocyte-mediated disease states or conditions, with the result of monocyte killing or impairment being dependent upon the effect desired by the treating physician. It is also to be understood that characterization of a disease state or condition as being autoimmune or inflammatory as with rheumatoid arthritis and multiple sclerosis can be a function of how one wishes to view the disease or condition because both autoimmunity and inflammation are present. Monocytes mediate both autoimmunity and inflammation, and the killing of monocytes or impairment of their function alleviates the symptoms of those diseases and conditions that monocytes mediate.

Any of the before-discussed methods can be carried out while the patient is continuing therapy with a previous drug or drugs, or after cessation of such prior treatment. When a patient is removed from a prior even partially effective treatment, a flare-up (exacerbation) of symptoms sometimes occurs that typically abates after several months. In addition, where a prior treatment regimen is halted while an above method is practiced, that prior treatment can be continued after cessation of an above method, often with quite positive results.

D. Compound Synthesis

A compound useful herein where Z is absent can be prepared by condensing an appropriately substituted adenine directly with an appropriately substituted sugar ring as by the techniques described in Montgomery et al., (1986) *J. Med. Chem.*, 29:2389–2392, by the method taught in U.S. Pat. No. 4,082,911, or as described in the citations of Herdewijn et al. (1987) *J. Med. Chem.*, 30:2131–2137, which disclosures are incorporated herein by reference. An appropriately substituted adenine can be prepared by following reported literature syntheses or analogous syntheses. Still further, Wright et al. (1987) *J.Org. Chem.*, 2:4617–4618 recently prepared 2-chloro- and 2-bromo-2'-deoxyadenosines by direct reaction of the appropriate 2,6-dihalo purine with a 3',5'-protected-alpha-1-chlororibose using sodium hydride in acetonitrile, followed by treatment with methanolic ammonia at 60 degrees C. to deprotect the resulting 3',5'-hydroxyls and form the 6-amino group of the finally produced adenosine. Fukukawa et al. (1983) *Chem. Pharm. Bull.*, 31(5):1582–1592 also report syntheses of 2'-deoxy-2'-arahalo-substituted adenosine derivatives.

The 2'-deoxy-2'-fluoroarabinofuranosyladenine compounds of the present invention are produced as described hereinafter in the Examples. The synthesis is similar to that taught in Marquez et al. (1987) *Biochem. Pharmacol.*, 36:2719–2722, herein incorporated by reference, in which 6-chloropurine is condensed with 3-O-acetyl-5-O-benzoyl-2-deoxy-2-fluoro-D-arabinofuranosyl bromide. The functionalized halosugar is produced according to the method reported by Reichman et al. (1975) *J. Carbohyd. Res.*, 42:233 and the 2'-deoxy-2'-fluoro-arabinofuranosyladenine compound is obtained by ammonolysis with concentrated methanolic ammonia which removes the protective groups. Syntheses of 2-substituted-2'-deoxy-2'arafluoroadenosines are also described in U.S. Pat. Nos. 4,918,179 and 5,034,518, whose disclosures are incorporated by reference.

The adenosine-1-N-oxide group of compounds, i.e, where Z is present, is of particular interest since those materials, per se, are most likely not incorporated into a growing polynucleotide chain because the presence of the N-oxide group probably interferes with hydrogen bonding during that synthesis. Rather, it is believed that the N-oxide compounds are reduced by an endogenous reductase prior to their incorporation into and termination of the growing chain.

Nevertheless, being free from a net ionic charge, but possessing an internal zwitterionic charge pair, the N-oxide compounds can penetrate cell membranes. Those compounds are also somewhat more water-soluble than are the corresponding un-oxidized compounds.

Without wishing to be bound by theory, it is nevertheless believed that the N-oxide compounds enter the cell and are phosphorylated, in keeping with the report of such phosphorylation in Lindberg et al. (1967) *J. Biol. Chem.*, 242:350–356. A pool of such derivatives is maintained intracellularly until such time as the N-oxide function is reduced and the nucleotide is incorporated to terminate the appropriate, growing polynucleotide chain.

The 1-N-oxide compounds are readily prepared by the method of Klenow et al. (1961) *Biochim. Biophys. Acta*, 52:386–389, with slight modification, as discussed hereinafter.

The present invention is further illustrated by the following examples which are not intended to limit the scope of the invention in any way.

EXAMPLE 1

Cytotoxicity of CdA In Vivo

The effect of 2-chlorodeoxyadenosine (CdA) administration upon the level of circulating peripheral blood monocytes, lymphocytes, neutrophils and platelets was determined as follows.

Eight cutaneous T-cell lymphoma patients were administered continuous intravenous infusion of a composition containing 2-chlorodeoxyadenosine at a dosage of 0.1 mg/kg of body weight per day in isotonic saline. Blood samples were obtained daily and the number of viable cells present were enumerated daily for seven days after treatment.

The average results obtained as to three cell types are illustrated in FIG. 1, which shows the enhanced toxicity of 2-chlorodeoxyadenosine toward blood monocytes. The mean level of monocyte decrease caused by contacting the monocytes with the CdA-containing composition at day 7 was 80 percent. Monocytes disappeared completely from the circulation of four of the eight lymphoma patients by the seventh treatment day.

Platelet and hemoglobin levels were constant over the time period shown. As is seen, no significant decrease in the number of circulating neutrophils was noticed, whereas the number of circulating lymphocytes decreased by 30 percent by the end of period of infusion of CdA. Monocyte numbers returned to approximately the pre-administration values within about two weeks after cessation of the CdA administration.

Thus, the present invention provides a method for decreasing the number of circulating blood monocytes. Similarly, it has been found that administration of 2-chlorodeoxyadenosine to autohemolytic anemia patients resulted in a significant decrease in autoantibody production and concomitant reduction in hemolysis.

EXAMPLE 2

Cytotoxicity of CdA In Vivo

Comparative cytotoxicity of 2-chlorodeoxyadenosine (CdA) to purified human monocytes, lymphocytes and human fibroblast cells was determined as follows.

Peripheral blood monocytes and lymphocytes were isolated by well known methods from normal subjects. The cells were cultured while fresh at a density of about $5 \times 10^5$ cells per ml in 96-well flat-bottomed tissue culture plates using a contacting composition containing RPMI 1640 medium supplemented with 2 mM L-glutamine, 50 µM 2-mercaptoethanol and 20 percent autologous plasma (complete medium), and further containing varying concentrations (0–125 nanomolar) of CdA over a five day culture period at a temperature of 37 degrees C. in air containing 5 percent $CO_2$. The human fibroblast cell line GMO1380 was obtained originally from the NIGMS Human Genetic Mutant Cell Repository, Camden, N.J., and cultured under the same conditions as above. That cell line was from a normal fetal lung.

Toxicity towards the monocytes and fibroblasts was determined by a modification of the MTT reduction assay described in Mosmann (1983) *J. Immunol, Meth.*, 65: 55–63. After culturing for up to five days, 3-(4,5-dimethylthiazol-2-yl)-2,5-diphenyl tetrazolium bromide (MTT) at 0.2 mg (40 µl) was admixed with each well and the incubation was continued for another 4 hours. The plates were then centrifuged at 1000×g for 10 minutes, and supernatants were carefully aspirated with a finely drawn pipette.

Acidified isopropanol (100 μl; using 0.04N HCl) was added to each well. The plates were sealed, shielded from light, and placed at −20 degrees C. for about 18 hours to permit complete dissolution of the blue formazan precipitates.

Viable cell numbers were determined using a Dynatech microplate spectrophotometer, measuring absorbance at a wavelength of 570 nanometers (nm), using a reference wavelength of 630 nm. The assay could detect as few as 2000 unactivated monocytes, and the absorbance of MTT formazan at 570 nm was linear with respect to the number of monocytes over a range of about $2.5–20\times10^3$ cells.

Toxicity of CdA towards cell lines and lymphocytes in suspension was determined by erythrosin B dye exclusion using standard techniques.

Figure 2:
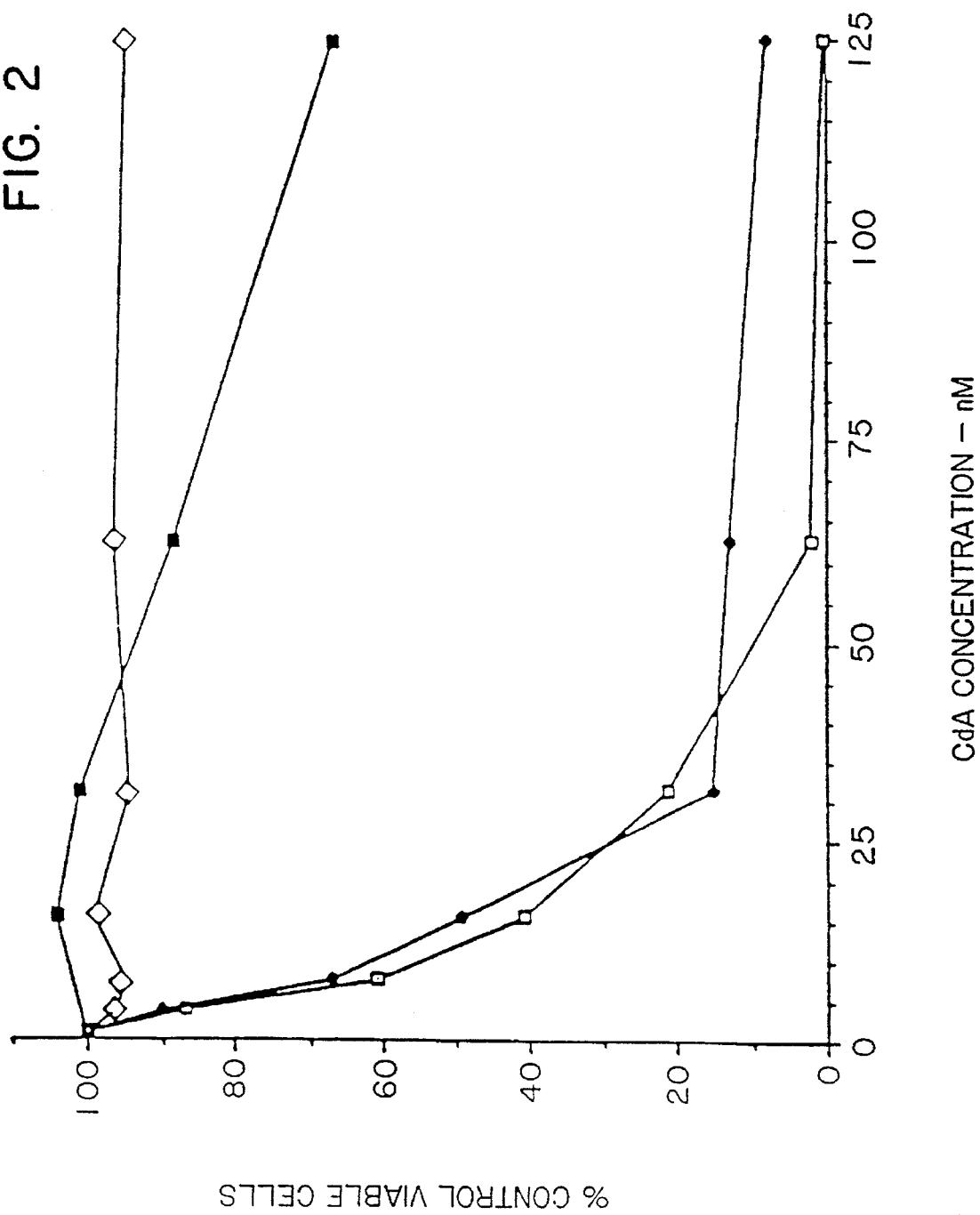
FIG. 2 is a graph illustrating the dose-response cytotoxicity of 2-chlorodeoxyadenosine (CdA) towards normal human monocytes (open squares), the human fibroblast cell line, GM01380, which is from normal fetal lung (open diamonds) and normal human lymphocytes (closed diamonds), when cultured in vitro. Cells were cultured in vitro as described in Example 2 for five days in the presence of varying concentrations of CdA from 0 to 125 nanomolar (nM), after which time viable cells were determined. The percentage of viable cells remaining after treatment (ordinate) is plotted against the concentration of CdA utilized (abscissa), on a linear scale. The effect of the presence of deoxycytidine (dCyd, 100 µM) on CdA toxicity toward monocytes (closed squares) is also illustrated.

Results of this in vitro cytotoxicity assay are shown in FIG. 2. Cytotoxicity is expressed as a percentage of viable cells remaining after five days of exposure to CdA in comparison with the number of viable cells after five days without any CdA added to the culture medium (VIABLE CELLS % OF CONTROL). Whereas 50 percent of the cultured monocytes were killed after five days exposure to 20 nM CdA, no appreciable toxicity was observed on the growth of fibroblast cells at the same CdA concentration. It was further noticed that monocyte sensitivity to CdA was substantially reduced by the presence of deoxycytidine (100 μM). This result appears to implicate deoxycytidine kinase activity in the cytotoxicity of CdA.

It should be emphasized that these results were unexpected. It has been found that the toxicity of CdA depends upon its phosphorylation and conversion to CdA-5'-triphosphate. The formation of CdA nucleotides is a function of the ratio between deoxycytidine kinase activity and 5'-nucleotidase activity. Because human macrophages were reported to have low deoxycytidine kinase levels, and appear to have ample 5'-nucleotidase, cells of the monocyte/macrophage lineage were not expected to exhibit sensitivity to CdA. Importantly, the concentrations of CdA that are toxic to monocytes in vitro are in the same range as those measured in the plasma of patients who currently receive CdA chemotherapy for chronic lymphoid malignancy.

Furthermore, because cells of the monocyte/macrophage lineage are responsible, in large part, for inflammatory responses, the results of this study indicate that compounds of Formula II can be used to selectively reduce the number of circulating, blood monocytes and thereby ameliorate inflammation.

This was confirmed by another study in which the freshly isolated monocytes matured in culture for two weeks. In vitro cultured monocytes exhibit several characteristics typical of differentiated macrophages. In this study, 50 percent of freshly isolated monocytes were killed at a CdA concentration of 22 nM (in agreement with the results shown in FIG. 2, where there was 50 percent killing at 20 nM CdA). In contrast, 50 percent of 2 week old cultured monocytes were killed by a CdA concentration of greater than 250 nM, an increase in resistance of over 12.5 times. These data indicate that peripheral blood monocytes are much more sensitive to CdA than are differentiated macrophages, represented by the in vitro cultured monocytes. As such, CdA therapy affords a level of selectivity in that monocytes and not resting macrophages are preferentially killed. Nevertheless, inasmuch as macrophages mature from monocytes, the killing of monocytes ultimately results in a reduction of macrophages.

EXAMPLE 3

In Vitro Cytotoxicity of CdA Toward Monocytes

Freshly isolated human monocytes were cultured at a concentration of $10^5$ cells/well in 96-well flat-bottom tissue culture plates. The cells were incubated in complete medium (Example 2) for about 12 hours following initial plating. The cells were then treated by the addition of various concentrations of CdA to form monocyte-containing compositions specific wells and the plates were incubated, as discussed previously.

Figure 3:
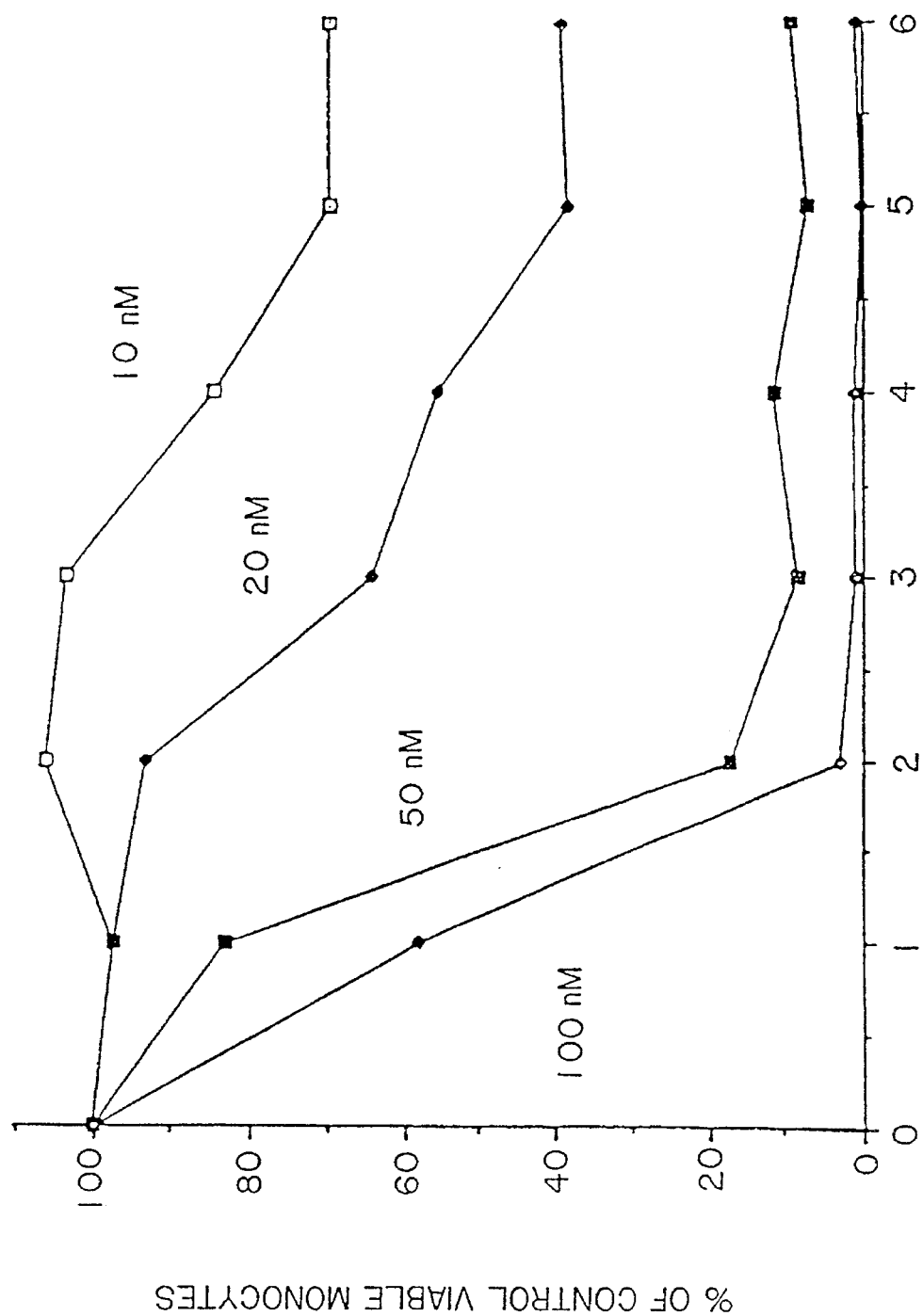
FIG. 3 is a graph of the dose- and time-dependence of 2-chlorodeoxyadenosine (CdA) cytotoxicity toward human monocytes in vitro.

The percentage of viable cells that were present in wells containing the treated monocytes was determined daily for six days. The results are illustrated in FIG. 3, which shows that CdA is toxic to monocytes and produces a significant decrease in cell viability within two days of treatment with 50 nM CdA.

EXAMPLE 4

DNA Damage in Monocytes Exposed to CdA

Monocytes were plated as discussed previously, and were then contacted with compositions containing various concentrations of CdA. The amount of DNA damage in monocytes exposed to CdA was determined by the fluorescent assay for DNA unwinding in alkaline solution described by Birnboim and Jevcak (1981) Cancer Res., 41:1889–1892, modified to accommodate lower cell numbers (Thierry et al. (1985) Radiation Res., 102:347–358).

Figure 4:
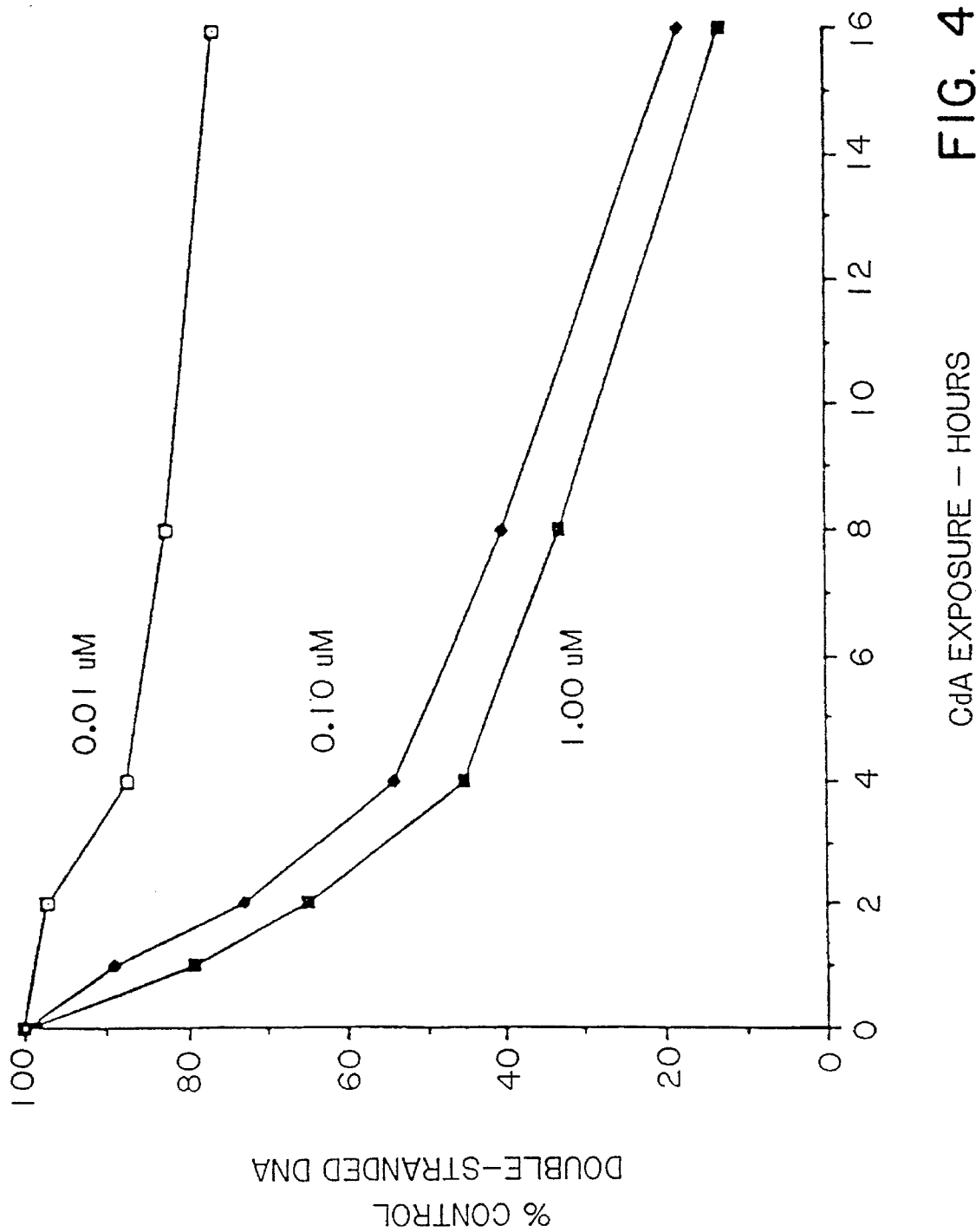
FIG. 4 is a graph of the dose- and time-dependence for CdA in inducing DNA strand breaks in monocytes in vitro.

The unwinding rate of DNA in alkaline solution at 15 degrees C. is proportional to the number of DNA strand breaks or alkali-labile sites. The ethidium bromide fluorescence of residual duplex DNA in samples exposed to pH 12.8 for one hour was compared to the fluorescence of a DNA aliquot that was not exposed to alkali. The percent residual double-stranded DNA at 1 hour was taken as a measure of the DNA damage in the sample. The results are illustrated in FIG. 4.

DNA breaks appeared within 2 hours in human monocytes exposed to 10 nM CdA, and accumulated with time during CdA exposure. The level of DNA damage was dose-dependent.

The repair of monocyte DNA damage caused by CdA was compared to the damage caused by gamma irradiation. Monocytes were pre-exposed to 0.1 or 1.0 μM CdA for four hours. At the end of this time, approximately 60 percent residual double-stranded DNA was present in the cells. The CdA was removed, and the amount of residual double-stranded DNA was calculated over the next four hours. Any increase in double-stranded DNA represents ongoing repair mechanisms.

Cells treated with 0.1 μM CdA contained an additional 10 percent residual double-stranded DNA over the next four hours; cells treated with 1.0 μM CdA showed no increase. In contrast, cells treated with gamma irradiation sufficient to cause a 60 percent reduction in double-stranded DNA (i.e., 40 percent residual double-stranded DNA) showed an additional 40 percent residual double-stranded DNA, to a total of 80 percent residual double-stranded DNA, over the next four hours. Therefore, the effects of CdA persist past the time of exposure, and the DNA damage caused by CdA exposure cannot be repaired as rapidly as an equivalent, or even greater, amount of damage caused by gamma irradiation.

EXAMPLE 5

Biochemical Effects of CdA in Human Monocytes

Cellular AND content was measured in human monocytes following incubation in culture with CdA (1 nM). An alcohol dehydrogenase cycling assay as described in Jacobson and Jacobson (1976) Arch. Biochem. Biophys. 175:627–634 was used to measure AND.

Monocytes, cultured and contacted as before described, were detached from the culture wells and were treated with perchloric acid (0.5M) for 10 minutes at 4 degrees C. The mixture was clarified and neutralized with KOH containing potassium phosphate buffer (0.33M) at pH 7.5. Monocyte ATP was quantitated in perchloric acid extracts by anion exchange HPLC, using a Whatman SAX column with an isocratic mobile phase consisting of $KH_2PO_4$ (0.25M), KCl (0.5M) and acetonitrile (2 percent) at pH 3.6 following the procedures of Carson et al. (1980) Proc. Nat'l. Acad, Sci. U.S.A., 77:6865–6869.

$NAD^+$ consumption for poly(ADP-ribose) synthesis is a known consequence of severe DNA damage in eukaryotic cells. To determine the potential role of NAD depletion in the marked toxicity of CdA towards monocytes, the temporal changes in oxidized AND and ATP in cells exposed to CdA at 1 nM were studied.

Figure 5:
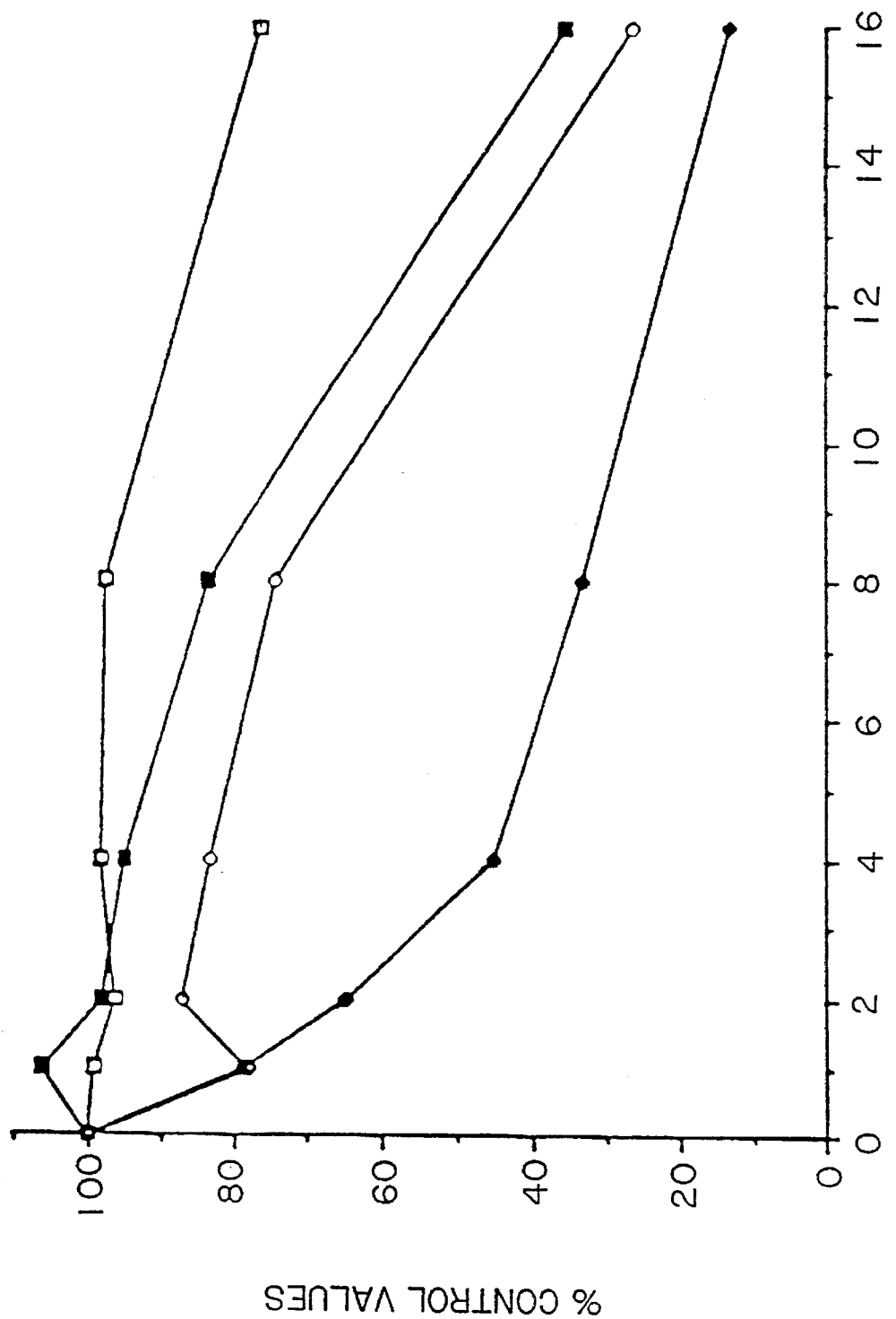
FIG. 5 is a graph showing the biochemical effects induced in human monocytes in vitro by exposure to 1 µM CdA over a period of 16 hours. The effects of CdA exposure upon monocyte viability (open squares), AND content (closed squares), RNA synthesis (open circles) and DNA strand breaks (ds-DNA; closed circles) are illustrated.

FIG. 5 shows the changes in oxidized AND in monocytes exposed to CdA. In contrast to measures of DNA integrity [double-stranded (ds)-DNA], the monocyte NAD content remained relatively constant during the first four hours of exposure, (>95 percent of control NAD), but declined progressively thereafter. The fall in NAD preceded the decreases in ATP and in cell viability that was first evident after a 16 hour exposure to CdA.

Monocyte RNA synthesis following CdA exposure was studied by measuring the incorporation of $^3H$-uridine. Monocytes were exposed to $^3H$-uridine (20 μCi/$10^6$ cells) during the final 1 hour of CdA (1 nM) exposure. Radioactivity measured was contained in trichloroacetic acid precipitates collected onto cellulose acetate filters and measured by liquid scintillation counting. FIG. 5 illustrates that 1 nM CdA caused a progressive reduction in RNA synthesis that was detectable after the first hour of culture, and was coincident with the appearance of DNA damage.

EXAMPLE 6

Monocyte Function Assays

Figure 6:
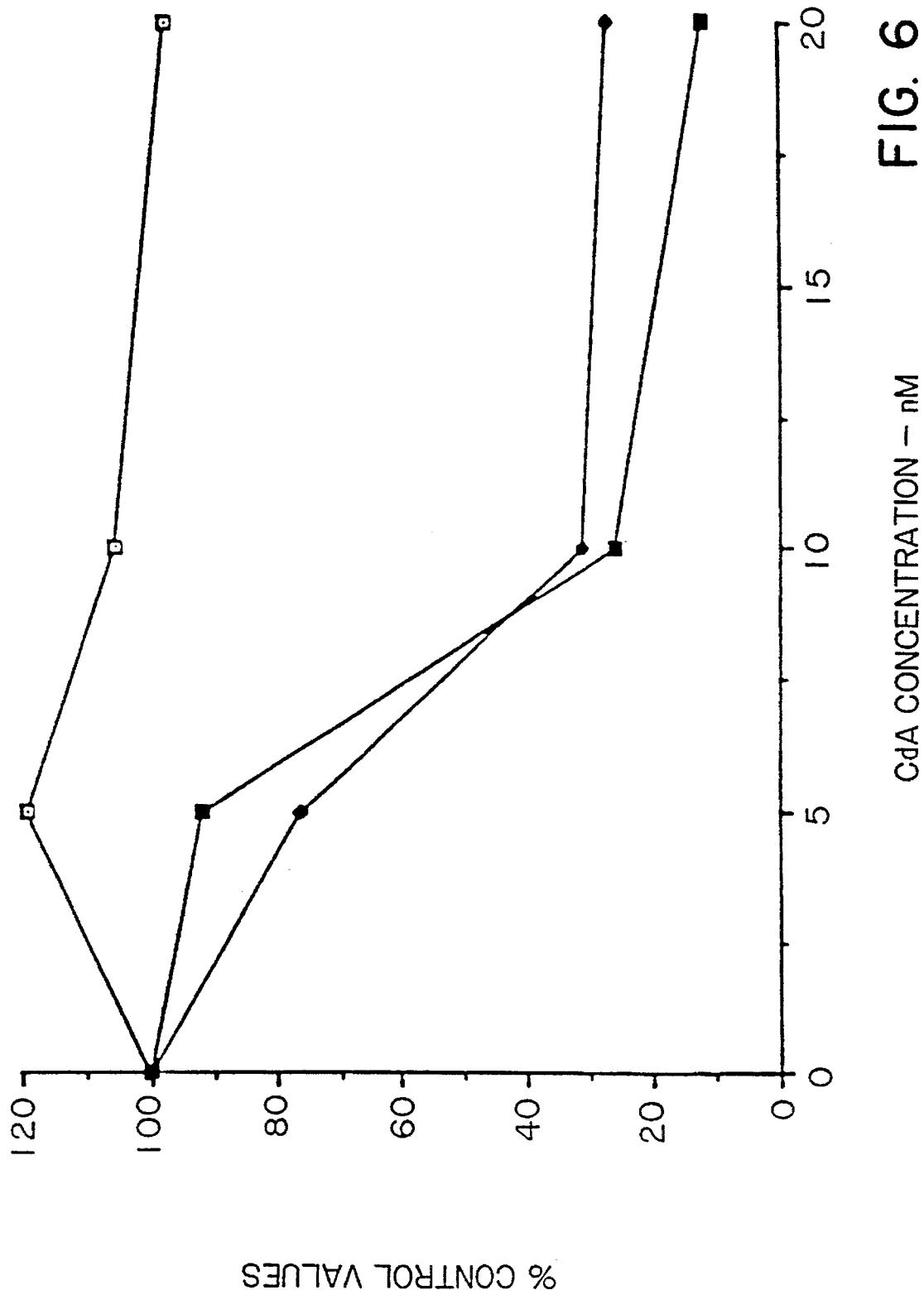
FIG. 6 is a graph that illustrates the effects of relatively low doses of CdA used to contact monocytes for a 72 hour time period. Monocyte release of interleukin-6 (IL-6; closed diamonds) and phagocytosis of antibody-coated red blood cells (RBC; closed squares) were examined, as was the viability of the cultured monocytes (open squares). Effects are expressed as a percentage of control values versus the CdA concentration in nanomoles (nM).

The effects of sub-lethal CdA concentrations on monocyte function in vitro was also studied. Cells were contacted and cultured with CdA (5–20 nM) for three days, after which phagocytosis and supernatant IL-6 activity were assayed. FIG. 6 shows that despite unchanged cell viability, the phagocytosis of antibody-coated erythrocyte targets was markedly suppressed by 10 and 20 nM CdA.

The ability of dialyzed culture supernatants to promote proliferation of B9.9 hybridoma cells is a measure of IL-6 activity (Helle et al. (1988) Eur. J. Immunol., 18:1535–1540). Monocytes spontaneously secrete IL-6 upon adherence to plastic during short-term in vitro culture (Guerne et al. (1989) J. Clin. Invest., 83:585–592). Monocytes cultured in autologous plasma 20 percent for three days secreted approximately 18 U per ml of IL-6, as determined by the bioassay standard curve using rIL-6.

FIG. 6 also shows that contacting monocytes with sub-toxic concentrations of CdA for three days inhibited the spontaneous secretion of IL-6 into the culture supernatant. At cytotoxic concentrations of CdA, however, supernatants contained high levels of IL-6, presumably due to cell lysis and release of the monokine from intracellular stores.

Monocyte phagocytosis was assayed using autologous erythrocyte targets, sensitized with a subagglutinating titer of rabbit anti-human erythrocyte IgG (Cappel, Malvern, Pa.). Monocytes ($2\times10^5$ cells/well) were exposed to sub-toxic concentrations of CdA in microwell plates for 72 hours. Complete medium was replaced with medium containing 10% fetal bovine serum, and a suspension of sensitized erythrocytes (0.25% packed cell volume) was added to the adherent monocyte layers. After incubation for 4 hours at 37 degrees C., the degree of phagocytosis was quantitated by the spectrophotometric method of Jungi (1985) J. Immunol. Meth., 82:141–153. This assay is based on the hemoglobin-catalyzed peroxidation of diaminobenzidine by detergent lysates of mononuclear phagocytes.

The spontaneous secretion, of IL-6 by cultured monocytes was measured by the hybridoma growth factor bioassay as described by Guerne et al. (1989) J. Clin. Invest., 83:585–592. In this assay, the proliferation of a B9.9 murine hybridoma subclone is dependent on the presence of IL-6. Supernatants collected from monocytes cultured up to 72 hours with CdA were first dialyzed to remove the compound, then diluted 1:12 into wells containing B9.9 cells from the IL-6 bioassay. In order to eliminate the stimulatory effects of contaminating lipopolysaccharide during monocyte isolation, polymyxin B (12.5 ug/ml) was added to reagents, buffers, and adherence media used to prepare cells for these studies.

EXAMPLE 7

Cytotoxicity of CdA In Vivo

A study similar to that described in Example 1 was carried out with three patients having rheumatoid arthritis. In each instance, the patient had been unsuccessfully treated with methotrexate, a gold salt or penicillamine, which treatment had been stopped three weeks prior to the first treatment with CdA. Although the prior treatments had been considered to be unsuccessful, the symptoms exhibited by the patients exacerbated prior to and during the initial CdA administration.

In this study, a composition containing CdA as discussed in Example 1 was administered to patients by infusion for a five-day time period in three cycles using about four to six weeks between treatment cycles.

Figure 7:
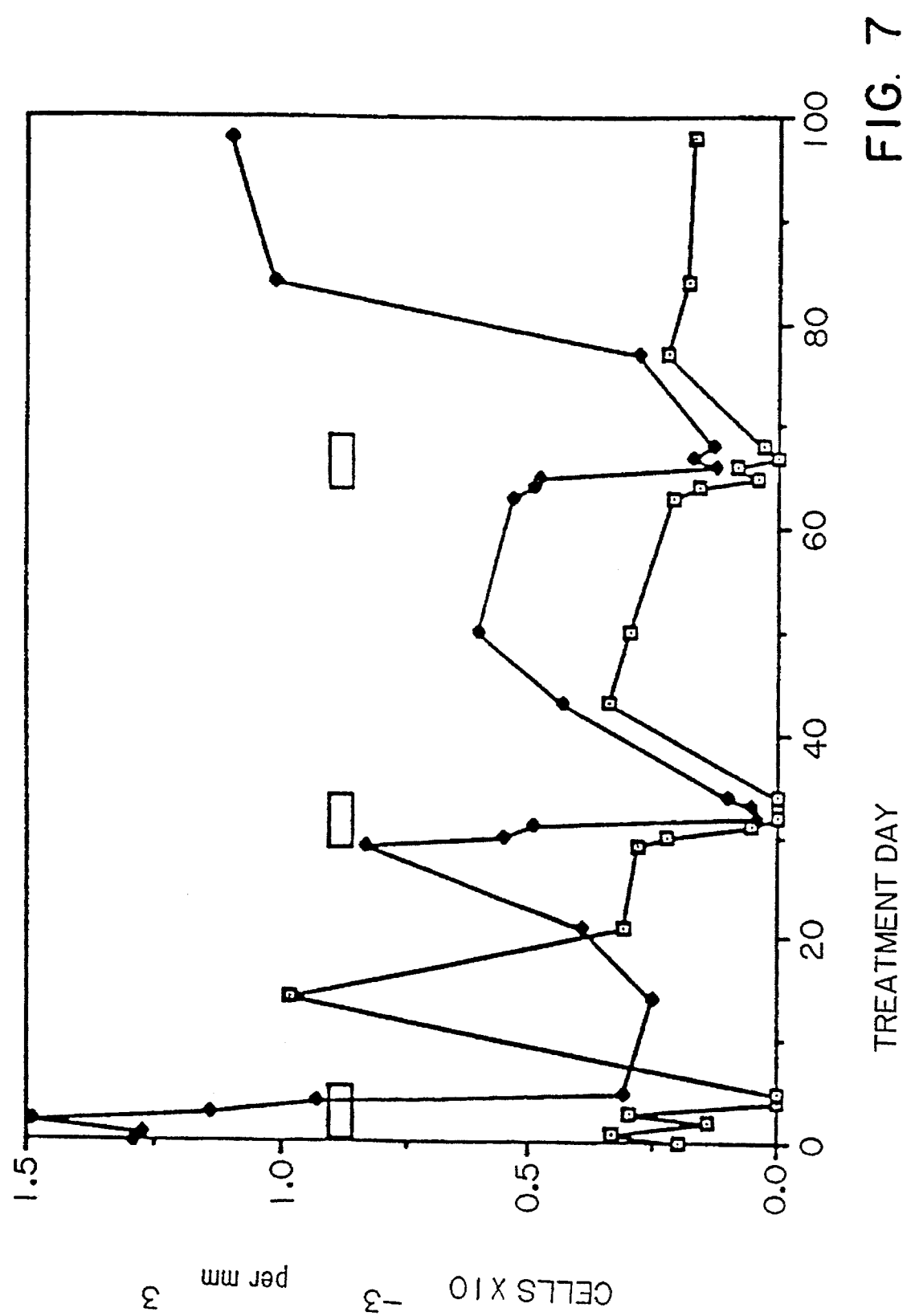
FIG. 7 is a graph showing the results of a study of the cytotoxicity of CdA toward monocytes and lymphocytes of a rheumatoid arthritis patient receiving CdA therapy. A continuous intravenous infusion of CdA (0.1 mg/ml in isotonic saline) was administered at a dosage of 0.1 mg/kg per day for a five-day period. Monocyte numbers are shown as open squares and lymphocyte numbers are shown as closed diamonds. Three cycles of infusions of CdA were given, and are illustrated as open rectangles for the five-day time periods of each infusion at a position in the graph above the days in the treatment regimen on which infusions were given.

Data for monocyte and lymphocyte cell numbers are shown in FIG. 7 for patient 1, a 63-year old woman with sero-positive rheumatoid arthritis. Neutrophil and platelet numbers were also assayed and were shown to be substantially constant throughout the one hundred days of the study. Similar results for three of the four cell types were obtained for patients 2 and 3. Patient 3 had a neutropenia temporally related to a viral syndrome, but which resolved after discontinuation of non-steroidal anti-inflammatory drug therapy. Cell numbers were assayed as discussed in Example 1.

As can be seen from FIG. 7, monocyte number dropped to substantially zero during each CdA administration cycle. Monocyte numbers then returned to approximately the original, pre-treatment, number within about ten days after infusion of CdA was stopped for each cycle.

Table I below displays the results of this study. A specially trained nurse examined the number of swollen and painful joints in each of the patients prior to the start of each treatment. The values obtained are as listed for each patient. A reduction in the number of painful or swollen joints is noted in two of the three patients involved in the study.

TABLE I

RHEUMATOID ARTHRITIS JOINT PARAMETERS DURING TREATMENT WITH CdA BY 5-DAY CONTINUOUS INFUSION AT MONTHLY INTERVALS

| Parameter | Pt. # | CdA Treatment Course (Months) | | | | | |
|---|---|---|---|---|---|---|---|
| | | 1 | 2 | 3 | 4 | 5 | 6 |
| Swollen Joints | 1 | 51/47 | 37 | 25 | | | |
| | 2 | 9 | 27 | 25 | 22 | 23 | 14 |
| | 3 | 16 | 17 | 14 | 11 | | |
| Painful Joints | 1 | 73/38 | 39 | 23 | | | |
| | 2 | 32 | 34 | 28 | 36 | 27 | 26 |
| | 3 | 36 | 40 | 54 | 59 | | |
| PIP Joint | 1 | 583 | 612 | 560 | | | |
| Measurement | 2 | 527 | 526 | 531 | 498 | 485 | 506 |
| (Totals, in mm) | 3 | 560 | 548 | 549 | 602 | | |
| Performance | 1 | 70 | 33 | 27 | | | |
| Index | 2 | 46 | 28 | 22 | | | |
| | 3 | 30 | 36 | 32 | | | |

PIP joint measurements refer to the total arthrocircameter measurements, in mm, of each proximal interphalangeal (PIP) joint, for each patient. Values are shown for each of the three patients.

Each patient was asked to rank his or her performance of nine function parameters on a 0 to 10 scale, 10 being the highest. These function parameters were: turning in bed, rising from a chair, buttoning buttons, combing hair, walking, turning knobs, climbing stairs, getting in and out of an automobile, and general well being. The total score on these nine parameters for each patient is listed as the performance index.

Upon completion of the above treatment regimen that was itself deemed successful, the patients returned to each of his or her prior treatment regimens. A total of twelve patients have now been treated, about one-half with a continuous infusion as the other one-half with intermittent infusion.

One of the inventors herein, Dr. Carson, has received follow-up letters from the personal physicians of each of three patients of the study whose results are shown in Table I. Two physicians reported a total white cell count drop from pretreatment values of about 50 percent that lasted about three years post treatment for one patient and over one year for the other. All three physicians reported that their patients' arthritic disease states had improved.

That improvement was noted in a significant decrease in morning stiffness and pain and succulent synovitis, and being much more ambulatory, for two patients. The third patient was referred to as being essentially in remission from the standpoint of her rheumatoid disease. The duration of those improvements was said to be for about one to one and one-half years after the CdA treatment stopped.

One of those physicians reported that those noted improvements were delayed by several months after the CdA treatment ceased, but were quite definite. That physician's patient dropped out of the study prior to its completion due to an overwhelming fatigue phenomenon that occurred after CdA treatment.

One of the patients had been treated with methotrexate and then Imuran prior to the CdA treatment, whereas another had been treated with methotrexate. Both were restarted on methotrexate after the CdA treatments stopped.

In summary comments as to the above three patients, one of the physicians reported that the clinical observation was that patients who received CdA treatments did quite well for a year or more following their trial. It seemed that their courses became favorable and that they had less joint complaints. In addition, those patients were better controlled on the regimens that they had been on prior to the trial.

Preliminary studies have also measured the concentration of interleukin-1β (IL-1β) in cryopreserved plasma samples from one of the rheumatoid arthritis patients. IL-1β is a lymphokine released by antigen-stimulated macrophages that promotes the formation of interleukin-2 in antigen-activated cytotoxic T cells. IL-2 promotes mitosis in activated cytotoxic T cells.

This patient received CdA, as before, in four treatments over a time period of almost 100 days. Each treatment was by 5-day continuous infusion.

IL-1β concentrations were measured using a commercially available ELISA kit (Cistron). The results showed a significantly lower IL-1β level on each last infusion day compared to the pretreatment values.

EXAMPLE 8

Treatment of Multiple Sclerosis with CdA

A study of four patients with chronic multiple sclerosis was undertaken. Each patient was first examined for normal hepatic, renal, and bone marrow functioning to establish baseline values. Each of the patients was then treated with CdA dissolved in sterile preservative-free isotonic saline. The CdA was administered intravenously at a dosage of 0.1 mg/kg each day for a total of seven days. Each patient received six courses of intravenous therapy, once monthly for a total of six months. Patients were examined on a daily basis while hospitalized. During that time, daily blood counts and twice weekly blood chemistries were performed on each patient. CdA levels were also measured in blood and spinal fluid.

The neurologic function of each of these patients was measured using the expanded Krutzke disability status scale (EDSS), and the neurologic rating scale (NRS).

There was no evidence of any significant toxic side effects. None of the four patients exhibited any nausea, vomiting, skin rash, or hepatic or renal dysfunction. Each of the patients developed lymphopenia (reduction in the level of lymphocytes in the blood), with absolute lymphocyte counts being suppressed 0.5 to about 10 percent for more than one year.

Monocyte levels dropped after each treatment. For example, in one patient, monocytes dropped 40 percent after the first treatment, and were substantially absent after each of the remaining five treatments. For another patient, monocytes were substantially absent after two treatments, and depleted by about 85, 50, 40 and 73 percents after the other four treatments.

In some cases, there was leukopenia (reduction in the level of total white blood cells). There was also a modest macrocytosis in all patients lasting for six to eight months after cessation of treatment. However, the platelet counts of all four patients remained within the normal range. In essence, there was no evidence of toxicity in these four patients with normal marrow, hepatic and renal functions. Likewise, the side effects of CdA were imperceptible in these four patients.

Measurement of neurologic function using the EDSS and NRS scales provided evidence of improvement in all four patients during treatment with CdA. Cerebrospinal fluid studies (CSF) showed a marked drop in lymphocyte counts and, quite remarkably, complete disappearance of IgG oligoclonal bonds in all cases. There was no significant change in total CFS IgG.

In particular, the NRS data demonstrated between 5 and 50 percent improvement from baseline pretreatment values in all patients. One of the four patients was completely bed-ridden at the beginning of the treatment, and this patient was able to walk with the aid of a walker by the end of the treatment. All patients reported subjective feelings of improved energy and stamina.

EXAMPLE 9

Reduction of Plasma Neopterin Levels by Treatment with CdA

Plasma neopterin levels were measured in a patient with rheumatoid arthritis. Neopterin is released from monocytes and macrophages activated in an immune response. Huber et al., *J. Exp. Med.*, 160:310–316 (1984). Likewise, high levels of neopterin are associated with clinical activity in patients with rheumatoid arthritis. Clinical activity was rated by the following criteria: duration of morning stiffness, range of motion, subjective pain score, measurement of grip strength, synovial thickening, and number of inflamed joints. Reibnegger et al., *Arthritis Rheum.*, 29:1063–1070 (1986). The levels of neopterin in patients with rheumatoid arthritis are proportional to both clinical activity and the levels of activated monocytes and macrophages in these patients.

In this study, a patient with rheumatoid arthritis received CdA by a weekly, four hour intravenous infusion at a dosage of 0.125 to 0.15 mg/kg body weight for an approximately three month course of therapy. Plasma neopterin levels were measured throughout this treatment regime.

These levels rapidly dropped from a value of about 60 nM plasma neopterin to about 25 nM plasma neopterin within the first seven days of therapy. Thereafter, plasma neopterin levels showed an approximately even amount of neopterin at about 30 nM for days 14 through 70 after the first administration, and then an increasingly downward trend, such that by about day 84 of therapy only about 18 nM plasma neopterin was detected.

These data provide further in vivo evidence that CdA acts by reducing the levels of activated monocytes and macrophages. Because activated monocytes and macrophages play a role in the pathology of rheumatoid arthritis, these data indicate that CdA is useful in the treatment of this monocyte-mediated inflammatory disease.

EXAMPLE 10

Effects of CdA on Antigen-Induced Arthritis in Rabbits

Antigen-induced arthritis in rabbits is an animal model of rheumatoid arthritis. In this model, the rabbits are sensitized to an antigen such as ovalbumin or methylated bovine serum albumin in an adjuvant. Several weeks later, the same antigen is injected directly into the joints of the animal. This results in a delayed-type hypersensitivity response in the joint, leading to a chronic arthritis that mimics rheumatoid arthritis. Histologically, the synovial lining of the rabbit joints shows a massive infiltration of inflammatory cells such as macrophages, small lymphocytes and plasma cells. Pettipher et al., *Br. J. Exp. Path.*, 69:113–122 (1988).

Rabbits with antigen-induced arthritis were treated with CdA (1 mg/kg), tepoxalin (25 mg/kg) or naproxen (5 mg/kg). Upon pathological examination of these joints following treatment, it was noted that the joints from animals treated with CdA exhibited a milder inflammatory response coupled with much less tissue damage compared to untreated controls. Tepoxalin provided similar results, whereas Naproxen appeared to exacerbate the inflammation and tissue destruction. CdA therefore greatly reduces the effects of this monocyte-mediated condition in an animal model of rheumatoid arthritis.

EXAMPLE 11

In Vitro Cytotoxicity of CAFdA Toward Selected Cell Lines seven different cell lines were treated with varying concentrations of 2-chloro-9,1'-beta-2'-deoxy-2'-fluoro-D-arabinofuranosyladenine (CAFdA) to determine percent viability. CAFdA concentrations ranging from 0 to about 260 nM were used to treat each cell line in vitro.

A B cell line, denoted SB, was least sensitive to the compound, with 90 percent viability when treated with about 260 nM CAFdA. A myeloid cell line, designated K562, was more sensitive than the SB cell line, with 40 percent viability at about 260 nM CAFdA.

Of the other five cell lines, two were T cell lines, one called CEM and the other Molt-4, and the remaining three were monocyte-like cell lines, designated THP-1, U937 and HL-60, respectively. These five cell lines all exhibited substantial sensitivity, with all five showing less than 20 percent viability at about 60 nM CAFdA, and less than 10 percent viability at concentrations above about 130 nM CAFdA. At dosages between about 25 and about 50 nM CAFdA, two monocyte-like cell lines, THP-1 and HL-60, and one of the T cell lines, CEM, displayed a greater sensitivity, with about 60 percent or less viability, than the other cell lines tested. Similar results were found for CdA in a companion study using some of the same and some different cell lines.

The two compounds, CdA and CAFdA, were also compared for in vitro activity against another group of human cell lines in a direct comparative assay. The results of that study are shown below in Table II.

TABLE II

| | $ID_{50}$ (nM)[1] | | |
|---|---|---|---|
| Cell Type[2] | CdA | CAFdA | CAFdA CdA |
| CEM, wild type | 21 | 67 | 3.1 |
| CEM, deoxyeytidine kinase deficient | 716,000 | 716,000 | — |
| CEM, Increased 5'-nucleoside | 60 | 126 | 2.1 |
| DHL9, wild type | 80 | 150 | 1.9 |
| DHL9, Increased ribonucleotide reduction | 4,000 | 6,000 | 15. |

TABLE II-continued

| | $ID_{50}$ (nM)[1] | | |
|---|---|---|---|
| Cell Type[2] | CdA | CAFdA | CAFdA CdA |
| Peripheral blood lymphocytes | 15 | 18 | 1.9 |
| Monocytes | 22 | 47 | 2.1 |

[1]Concentration that produced 50 percent reduction in all numbers after five days
[2]CEM cells are T lymphoblasts; DHL9 cells are lymphoblasts.

The results of these two studies indicate a similar toxicity profile for the two compounds, with CdA being of similar to slightly greater potency as compared to CAFdA.

EXAMPLE 12

Oral and IP Effects of CdA and CAFdA on Delayed-Type Hypersensitivity

Delayed-type hypersensitivity (DTH) is a cell-mediated immune response that typically takes longer than 12 hours to develop. In the guinea pig, a DTH reaction to an antigen can be established by first immunizing the animal with the antigen in an adjuvant such as Freund's complete adjuvant. Subsequent intradermal injection of the antigen causes no change for at least 10 hours, after which there is a gradual increase in erythema and swelling in response to antigen injection. This response peaks about at about 24 hours after challenge, then gradually subsides.

Histologically, the inflammatory response is characterized by intense inundation of the site with mononuclear cells, of which about half are lymphocytes and the other half monocytes. DTH is therefore an indicator of a monocyte-mediated immune reaction.

In one study, guinea pigs were sensitized to ovalbumin in adjuvant. The animals were then treated either orally or intraperitoneally with saline (control), dexamethasone (5 mg/kg), CdA (1 mg/kg) or CAFdA (1 mg/kg). The animals were then injected with ovalbumin intradermally to elicit the DTH response. The mean area of the swelling size was measured for each animal (nine or ten animals were treated for each protocol).

Both dexamethasone and CAFdA, regardless of the route of administration, showed a significant inhibition of swelling at both 24 and 48 hours after ovalbumin challenge compared to control saline treated animals (p<0.01 by Student's t-test). CdA, on the other hand, was ineffective when given by the oral route, indicating the desirability of use of an enteric coating for oral administration, but caused significant inhibition of swelling compared to control animals when given intraperitoneally (p<0.01 by Student's t-test).

In another study, the effects of different dosages of CdA on the DTH reaction were examined. Guinea pigs sensitized to ovalbumin were treated with saline (control), dexamethasone (5 mg/kg), and CdA at 1 mg/kg or 0.1 mg/kg. Three days after treatment, the animals were challenged with ovalbumin intradermally. The areas of the skin lesions were measured at 6, 24, and 48 hours after challenge.

All three doses of therapeutic agents were effective at inhibiting swelling at 24 and 48 hours post-challenge when compared to control saline treated animals (p<0.01 by Student's t-test). The numerical values of the areas of swelling were lower in the CdA treated animals at both dosages when compared to dexamethasone-treated animals. The numerical values for 0.1 and 1.0 mg/kg CdA were substantially the same, and were slightly less than the value obtained with dexamethasone.

EXAMPLE 13

Synthesis of 2-chloro-9-1'-beta-2'-deoxy-2,-fluoro-D-arabinofuranosyladenine

1',3'-Di-O-acetyl-5'-O-benzoyl-2'-fluoro-beta-D-arabinose (4.7 gm, 13.8 mmol) is added to 1M $HBr/CH_2Cl_2$ at zero degrees C., then maintained at 5 degrees C. for 24 hours. The solvent is removed by rotoevaporation under negative pressure, and the dry product is dissolved in dry toluene. The product is dried by rotoevaporation under reduced pressure to yield 3'-O-acetyl-5'-benzoyl-2'-deoxy-2-fluoro-D-arabinofuranosyl bromide (ABFA).

ABFA is dissolved in 200 ml of dichloroethane. 2,6-Dicholoropurine (2.61 gm, 13.8 mmol) is added to the ABFA solution and the mixture is heated under reflux at 100 degrees C. for 16 hours. The solution is then filtered and rotoevaporated to dryness under reduced pressure. The dried power is dissolved in $CHCl_3$ and purified by flash chromatography (200 gm silica gel, 230–400 mesh, elution with 2:1 cyclohexane-ethyl acetate) to yield 2,6-dicholor-9,1'-(3'-O-acetyl-5'-O-benzoyl- 2'-deoxy-2'-fluro-beta-D-arabinofuranosyl)-9-purine. This 2'-fluoro-arabinofuranosyl derivative of 2,6-dichloropurine is reacted with methanolic ammonia to produce a 2-chloro-9-beta-2'-deoxy-2'-fluoro-D-arabinofuranosyladenine.

Thereafter, the solvent is removed by rotoevaporation and the resulting residue is washed by stirring in cold (4 degrees C.) water (20 ml). The product is collected by filtration. The major product is purified by flash silica cola chromatography (EtOAc: Methyl alcohol at 20:1), concentrated to a white powder by rotoevaporation and identified by NMR as 2-chloro-9,1'-beta-2'-deoxy-2'-fluoro-D-arabinofuranosyladenine.

A similar result is obtained by reaction of ABFA (above) with 2,6-dichloropurine in sodium hydride/acetonitrile as discussed in Wright et al., *J. Org. Chem.*, 52:4617–4618 (1987), followed by reaction with methanolic ammonia, as discussed above.

EXAMPLE 14

Synthesis of 2'-deoxyadenosine-1-N-oxide

2'-Deoxyadenosine (30 micromoles) in 5 ml of $NH_4HCO_3$ at pH 5.5 was admixed with 120 mmoles of the magnesium salt of monoperphthalic acid at a temperature of zero degrees C. with continuous mixing.

After a time period of 12 hours, the mixture was lyophilized, dissolved in 2 ml of water and applied to the top of a 20 ml chromatography column of Dowex AGlX-8 (formate form).

The 1-N-oxide was eluted with 0.1M $NH_4HCO_3$.

EXAMPLE 15

Compressed Tablet

| Ingredient | Amount. mg/Tablet |
| --- | --- |
| 2-Chloro-9,1'-beta-2'-deoxy-2'-fluoro-D arabinofuranosyladenine | 1 |
| Dibasic Calcium Phosphate NF | q.s |
| Starch USP | 40 |
| Modified Starch | 10 |
| Magnesium Stearate USP | 1–5 |

EXAMPLE 16

Hard Shell Capsule

| Ingredient | Amount. mg/Capsule |
| --- | --- |
| 2-Methyl-9',1'-beta-2'-deoxy-2'-fluoro-D arabinofuranosyladenine | 1 |
| Lactose, Spray Dried | q.s |
| Magnesium Stearate USP | 1–10 |

EXAMPLE 17

Oral Liquid (Syrup)

| Ingredient | Amount. % wt./vol. |
| --- | --- |
| 2-Hydroxy-9,1'-beta-2'-deoxy-2'-fluoro-D arabinofuranosyladenine | 0.5 |
| Liquid Sugar | 75.0 |
| Methyl Paraben USP | 0.18 |
| Propyl Paraben USP | 0.02 |
| Flavoring Agent | q.s. |
| Purified Water, q.s. ad | 100.0 |

EXAMPLE 18

I.V. Injectable Solution Concentrate

| Ingredient | Amount. % wt./vol. |
| --- | --- |
| 2-Chloro-9,1'-beta-2'-deoxy-adenosine-1-N-oxide | 0.1 |
| Benzyl Alcohol NF | 0.9 |
| Purified Water | 100.0 |

EXAMPLE 19

Enteric Coated Adenine Derivative

Table 1 lists the components of a drug composition of the present invention (Composition A) and an enteric coating composition (Composition B).

TABLE 1

| Ingredient | Weight |
| --- | --- |
| Composition A | |
| 2-Chloro-9,1'-beta-2'-deoxyadenosine | 67.0 |
| Polyvinylpyrrolidone | 1.3 |
| Modified Starch | 5.0 |
| Sodium Bicarbonate (anhydrous) | 20.0 |
| Citric Acid | 6.7 |
| | 100.0 |
| Composition B | |
| Chloroform | 66.4 |
| Methanol (anhydrous) | 15.4 |
| Cellulose Acetate Phthalate | 7.2 |
| Talc #127 U.S.P. | 7.3 |
| FD & C #5 Yellow | 1.0 |
| Diethyl Phthalate | 2.7 |
| | 100.0 |

The ingredients listed for Composition A are mixed, together with the slow addition of anhydrous isopropyl alcohol (700 ml per kg of Composition A) for about 9 to 15 minutes. The resulting blend is then segmented into tablets by extrusion. These segmented particles are dried in an oven at 35 degrees C. for about 40 to about 48 hours. The dried granules are sized through a 14 mesh screen. Those segments that pass through the screen are compressed in a tablet machine to produce tablets about 4.8 mm in diameter and about 4 mm thick.

The dried tablets are then coated with the pH sensitive enteric coating composition (Composition B) in a pan employing about 0.45 liters of Composition B per kilogram of tablets to give a uniform coating weighing about 5.5% by weight of the final tablet. The wet coated tablets are then dried.

The foregoing description and the examples are intended as illustrative and are not to be taken as limiting. Still other variations within the spirit and scope of this invention are possible and will readily present themselves to those skilled in the art.

What is claimed is:

1. A method of treating a monocyte-mediated inflammatory disorder in a mammal comprising:

administering to said mammal a composition containing a therapeutically effective dose of a 2-halo-2'-deoxyadenosine as an active ingredient dissolved or dispersed in a physiologically tolerable carrier, said 2-halo-2'-deoxyadenosine being administered in an amount sufficient to decrease the level of monocytes in the blood of said mammal by at least about 50 percent during the course of said treatment.

2. The method according to claim 1 wherein said 2-halo-2'-deoxyadenosine is 2-chloro-2'-deoxyadenosine.

3. The method according to claim 1 wherein said 2-halo-2'-deoxyadenosine is administered in an amount of about 0.04 to about 0.20 milligrams per kilogram of body weight per day.

4. The method according to claim 1 wherein said administration is repeated periodically.

5. The method according to claim 1 wherein said administration is parenteral.

6. A method of treating a monocyte-mediated inflammatory disorder in a mammal comprising:

administering to said mammal a composition containing a therapeutically effective dose of a 2-chloro-2'-deoxyadenosine as an active ingredient dissolved or dispersed in a physiologically tolerable carrier, said 2-chloro-2'-deoxyadenosine being administered parenterally in an amount sufficient to decrease the level of monocytes in the blood of said mammal by at least about 50 percent during the course of said treatment.

7. The method according to claim 6 wherein said 2-halo-2'-deoxyadenosine is administered in an amount of about 0.04 to about 0.20 milligrams per kilogram of body weight per day.

8. The method according to claim 6 wherein said administration is repeated periodically.

9. The method according to claim 6, wherein said parenteral administration is by intravenous infusion.

* * * * *